Figure 1:
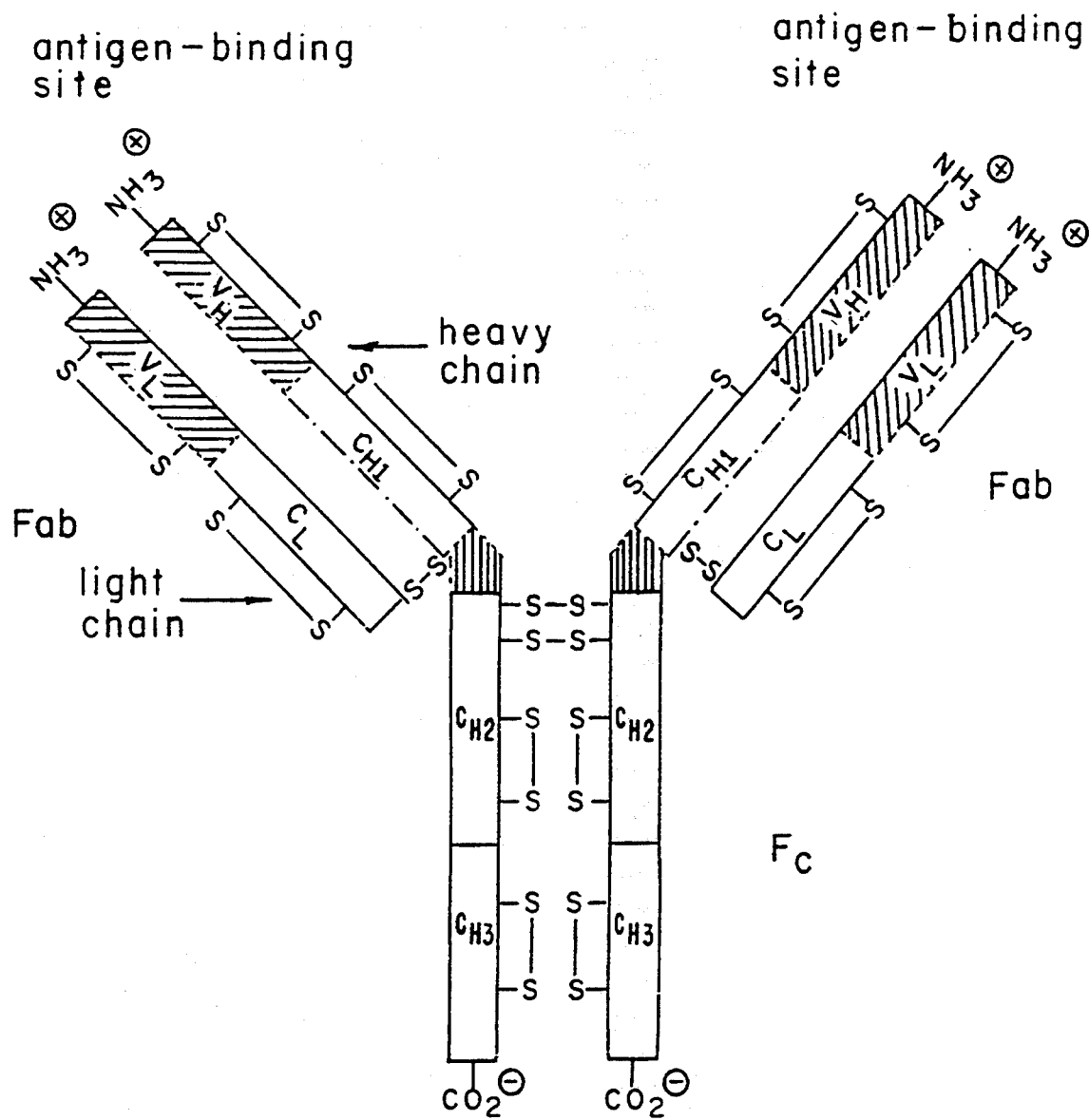

United States Patent [19]

Benkovic et al.

[11] Patent Number: 5,439,812
[45] Date of Patent: Aug. 8, 1995

[54] ANTIBODIES CATALYZING DEAMIDATION OF PROTEINS

[75] Inventors: Stephen J. Benkovic; Scott D. Taylor; Richard A. Gibbs, all of State College, Pa.

[73] Assignee: The Pennsylvania Research Corporation, University Park, Pa.

[21] Appl. No.: 865,216

[22] Filed: Apr. 8, 1992

[51] Int. Cl.$^6$ .................... C12N 9/00; C12N 9/82; C12P 13/14
[52] U.S. Cl. .................... 435/109; 435/188.5; 435/229; 530/388.9; 530/389.8
[58] Field of Search .................... 435/188.5, 229, 109

[56] References Cited

U.S. PATENT DOCUMENTS 5,079,152  1/1992  Benkovic et al. .................... 435/125

OTHER PUBLICATIONS

R. A. Lerner, et al., Science, vol. 252, pp. 659–667 (1991).
G. Kohler, et al., Nature, vol. 256, pp. 495–497 (1975).
A. B. Robinson, et al., Curr. Top. Cell. Regul., vol. 8, pp. 247–295 (1974).
F. Fonseca-Wollheim, Clin. Chem., vol. 36/8, pp. 1483–1487, (1990).
J. Kyte, et al., J. Mol. Biol., vol. 157, pp. 105–132, (1982).
L. Sastry, et al., Proc. Nat'l. Acad. Sci. USA, vol. 86, pp. 5728–5732 (1989).
W. D. Huse, et al., Science, vol. 246, pp. 1275–1281 (1989).
M. Better, et al., Science, vol. 240, pp. 1041–1043 (1988).
A. S. Kang, et al., Proc. Nat'l. Acad. Sci. USA, vol. 88, pp. 4363–4366 (1991).
Liottz, L. J., et al., (1993) J. Am. Chem. Soc. 115, 350–351.
Gibbs, R. A., et al. (1992) Science 258, 803–805.

Primary Examiner—Charles L. Patterson, Jr.
Attorney, Agent, or Firm—Thomas J. Monahan

[57] ABSTRACT

A hapten is described which may be used to elicit antibodies that catalyze the deamidation of asparginyl-glycyl dipeptides to form two products, the isoaspartyl-glycyl dipeptide and the aspartyl-glycyl dipeptide. A general synthetic scheme is also presented which shows how to modify the hapten to provide specificity for a particular protein in the antibodies that are elicited by the (modified) hapten. Antibodies which catalyze the the deamidation reaction are also described.

18 Claims, 18 Drawing Sheets

Hapten RG2

Scheme I

Scheme I (continued)

|  | slope, OO/min |
|---|---|
| 2E4 + substrate | $1.49 \times 10^{-3}$ |
| Hapten + substrate | $2.96 \times 10^{-4}$ |
| 2E4 + hapten + substrate | $3.77 \times 10^{-4}$ |

|  | slope OO/min |
|---|---|
| 24C3 + substrate | $6.46 \times 10^{-4}$ |
| 24C3 + substrate + hapten | $3.23 \times 10^{-4}$ |

FIGURE 14

14A

```
                                                  λLc1
                        EcoRI                     Ribosome Binding Site              Met Lys Tyr
5'      TCGA ATTC TAAA CTAG TCGC CAAG GAGA CAGT CATA ATG AAA TAT
3'      AGCT TAAG ATTT GATC AGCG GTTC CTCT GTCA GTAT TAC TTT ATA
                                                                    Pel B Leader
        Leu Leu Pro Thr Ala Ala Ala Gly Leu Leu Leu Leu Ala Ala Gln Pro
        CCT ATT GCC TAC GGC AGC CGG CTG GAT TGT TAT TAC TCG CGG CCC AAC
        GGA TAA CGG ATG CCG TCG GCC GAC CTA ACA ATA ATG AGC GCC GGG TTG NcoI              SacI                        XbaI           NotI
        Ala Met Ala Gly Glu Leu                  stop stop
        CAG CCA TGG CCG GCC GAG CTC GTC AGT TCT AGA GTT AAG CGG CCG     3'
        GTC GGT ACC GGC CGG CTC GAG CAG TCA AGA TCT CAA TTC GCC GGC     5'
                                                              (SEQ ID NO:25)
```

14B

```
                                                  λHc2
                NotI                              Ribosome Binding Site              Met Lys Tyr Leu Leu
5'      GGCC GC AATT CTAT TTCA AGGA GACA GTCA TAAT GAAA TAC CTA TTA
3'       CG CGTT AAGA TATA AGTT CCTC TGTC AGTA TTAC TTT ATG GAT AAT
                                                                                                       NcoI
        Pro Thr Ala Ala Ala Gly Leu Leu Leu Leu Ala Ala Gly Pro Ala Met
        CCT ACG GCA GCC GGC TGG GAT TGT TAT TAC TCG CGG CCA CCA GCC A
        GGA TGC CGT CGG CCG ACC CTA ACA ATA ATG AGC GCC GGT GGT CGG T
                                                SpeI
                                    XhoI
        Ala Gln Val Lys Leu Leu Glu           Tyr Pro Ala Met Asp
        GCT CAG GTG AAA CTG CTC GAG CTC TAG ACT AGT TCT AGA TCA ACG GT
        CGA GTC CAC TTT GAC GAG CTC GAG ATC TGA TCA AGA TCT AGT TGC CA
                                                              EcoRI
        Val Pro Asp Tyr Gly Ser stop
        ACG TTC CGG ACT ACG GTT CTT AAT AGA ATT CG            3'
        TGC AAG GCC TGA TGC CAA GAA TTA TCT TAA GC AGCT       5'
                                                              (SEQ ID NO:27)
```

ANTIBODIES CATALYZING DEAMIDATION OF PROTEINS

BACKGROUND AND FIELD OF THE INVENTION

1. Field of the Invention

The invention is generally directed to the field of catalytic antibodies, in particular antibodies catalyzing the deamidation of proteins, and haptens for the induction and/or screening of such antibodies, and the use of such antibodies to catalyze the deamidation of proteins.

2. Background of the Invention

Advances in the fields of catalytic chemistry and immunochemistry have recently led to the tapping of the immune system to produce antibodies with a specific important function, catalysis of specific chemical reactions. This new technology provides the potential to customize highly selective catalysts for potential uses in various fields of biology, chemistry and medicine.

A fundamental concept in catalysis is the transition-state theory. According to this theory, a chemical reaction can be visualized in terms of the free energy changes of the reactants as a function of a reaction coordinate. The reaction coordinate having the highest free energy is the most unstable chemical species, termed the "transition state". Enzymes are now understood to accelerate chemical reactions by enlisting their binding energy to stabilize activated species undergoing chemical transformation, by which manner enzymes provide a pathway of lower free energy for the reaction mechanism.

Meanwhile, advances in immunochemistry have led to a better understanding of the nature of antibodies, and methods for the production of specifically desired antibodies. Antibodies are large proteins consisting of four polypeptide chains: specifically two identical heavy chains and two identical light chains. The light chains are divided into two domains, variable ($V_L$) and constant ($C_L$), while the heavy chains consist of four domains ($V_H$, $C_{H1}$, $C_{H2}$, and $C_{H3}$). The structure of an antibody is shown schematically in FIG. 1. Antibodies bind to ligands by means of a combining site comprised of a hypervariable region which consists of six loops of extended chains, three each from the light- and heavy-chain variable domains. The hypervariability of these regions provides the immune system with the ability to generate a large number of ligand-specific antibodies having a variety of binding characteristics.

About forty years ago, it was first pointed out by Pauling that the fundamental processes which determine binding of enzymes and antibodies are the same. Both achieve binding by the use of ordinary forces which occur when small molecules come within a few angstroms of each other. Of course, there are specific differences between enzymes and antibodies, but the similarity in binding specificity has led to the advance of catalytic antibodies as specific compounds for catalysis.

The potential of the immune system to perform chemistry was clearly recognized in 1986 when Schultz and Lerner first showed that antibodies raised to tetrahedral, negatively-charged phosphate and phosphinate transition state analogues could selectively catalyze the hydrolysis of carbonates and esters, respectively. Phosphinate and phosphonamidate analogues are thought to closely mimic the transition states for ester and amide hydrolysis, respectively, and have been used to design antigens for production of catalytic antibodies.

Since that time, antibodies have been generated which catalyze a wide variety of chemical reactions ranging from paracyclic to peptide bond cleavage, and including specifically antibodies which catalyze carbonate hydrolysis, ester hydrolysis, amide hydrolysis, Claisen rearrangement, amide bond formation, lactonization, transesterification and photo-induced cleavage (see for example Lerner, et al., Science 252:659 (1991) hereby incorporated by reference). The specificity of such antibody-catalyzed reactions has been shown to equal or even exceed that of the corresponding enzymatic reactions.

One of the challenges in this field is the design of an appropriate antigen which can mimic the transition state compound of the reaction of interest. The antigen must, of course, first induce antibodies which can catalyze the reaction of interest. But the antigen must induce antibodies which have a greater stabilizing interaction with reaction intermediates than with either the reactant or product in order to avoid non-catalytic stoichiometric complexes. Enzymes are particularly adapted to exert precise stereo-chemical control over the reactions which they catalyze. Antibodies, being ligand (antigen) specific, should also be able to catalyze stereo-selective reactions, provided proper attention is successfully paid to the symmetry between antigens and substrates. Early attempts to prepare catalytic antibodies were not successful, apparently in large part due to a failure to properly address the mechanistic requirements of the chemical transformation under study.

An important recent advance in immunology involves the preparation of monoclonal antibodies, for example as described by Kohler and Milstein (Nature 256:495 (1975)). These authors demonstrated that it was possible to generate monoclonal antibodies which consist of a single distinct molecular structure, thereby generating large amounts of homogeneous antibodies with desired specificity. According to this procedure, after an immunogenic response to a desired immunogen is achieved, antibody-producing plasma cells from, for example, the spleen are fused or hybridized to an immortal myeloma cell line. This enables the antibody-producing cells to be cultured in vitro indefinitely. Hybridomas can then be cloned and separated into colonies which produce a single antibody, With the resulting cells being screened for their ability to generate antibodies with the desired specificity and high affinity to the ligand of interest.

Immunogenic responses in the preparation of monoclonal antibodies have also been successfully accomplished with haptens. Haptens are small molecules which are not themselves immunogenic. Immunogenic response, however, can be stimulated if the haptens are coupled to an antigenic carrier molecule. Various coupling molecules can be utilized as known in the art, but particularly preferred molecules for use as carriers are the proteins bovine serum albumin (BSA) and keyhole limpet hemocyanin (KLH). Haptens coupled to BSA and KLH stimulate the production of monoclonal antibodies having specificity for the hapten of interest.

As a result, one approach which has developed for generating antibodies that catalyze a specific class of reactions is by synthesis of a hapten structure which mimics the transition state structure of the reaction to be catalyzed. A first experimental demonstration of this notion related to acyl transfer reactions, specifically simple hydrolytic reactions. Relatively stable phosphate, phosphinate and phosphonamide species were prepared to provide the transition state analogues, and antibody specific for the transition state analogues acted as catalysts with rate accelerations on the order of $10^3$ to $10^4$ over uncatalyzed reactions (See for example, Lerner et al., above).

There are now some 50 reactions that are known to be catalyzed by antibodies. At least conceptually, the most susceptible reactions to antibody catalysis would be a class of reactions, originally viewed as "no mechanism" reactions. Claisen rearrangement and Diels-Alder addition are two such examples.

One additional specific reaction receiving recent attention is deamidation. Deamidation of proteins is a process wherein the gamma-amino groups of asparagine or glutamine are lost to produce aspartic acid and glutamic acid, respectively. Generally, deamidation has profound affects of the folding of a protein and is a principle cause of irreversible denaturation. In some cases deamidation increases susceptibility of the protein to proteolytic degradation. Non-enzymatic deamidation is a slow process under physiological conditions. In the cases where the rate has been measured, the half-time of the reaction ranges from 8 to 80 days for proteins and from 6 to 277 days for peptides. Robinson and Rudd (Curr. Top. Cell. Regul., 8:248 (1974)) reviewed peptide and protein deamidation, and discussed possible roles for this reaction, in vivo. Subsequent research suggests that deamidation of aspargine (Asn) and glutamine (Gln) may be more widespread than initially thought. The existence of an enzyme which recognizes and modifies one of the products of non-enzymatic deamidation supports proposals that this post-translational modification plays a role in physiological processes. Deamidation is fundamentally a hydrolytic reaction, formally similar to the peptide-bond cleavage reaction, which is catalyzed by proteases. A schematic representation the mechanism for acid- and base-catalyzed deamidation reactions is shown below:

Cytochrome C (horse heart)
Dihydrofolate reductase (recombinant)
Glucagon
Hemoglobin Providence (human)
Hemoglobin Singapore (human)
Hemoglobin Wayne (human)
Insulin (human, bovine)
Lysozyme
Ribonuclease A (bovine)
Ribonuclease (bovine seminal)
Trisephosphate isomerase (human)
Trypsin (bovine)
Trypsin inhibitor (bovine) (human)
Tryptophan synthase
Adrenocorticotropin (porcine, ovine, human)
Alcohol dehydrogenase (Drosophila)
Aldolase (rabbit muscle)
Amyloid serum protein (human)
Calbindin (recombinant)
Chloroperoxidase (Caldariomyces fumago)
Cholera toxin B chain
Crystallin$\alpha$A (human)
Crystallin$\alpha$A (chicken)
Crystallin$\alpha$B$_2$ (bovine)
Crystallin$\beta$B$_p$(bovine)
Crystalline(duck)
Epidermal growth factor
F$_2$ coat protein
Growth hormone (human)
Growth hormone (bovine)
Histone H4 (human)
Hypoxanthine-guanine phosphoribosyltransferase
Immunoglobulin λ chain (mouse)
Interleukin$\alpha$1 (human)
Myelin basic protein (bovine)
Neocarzinostatin
Ovalbumin
Parathyroid hormone (human)
Prolactin (ovine, bovine)
Ribonuclease U$_2$ (Ustilago sphaerogena)

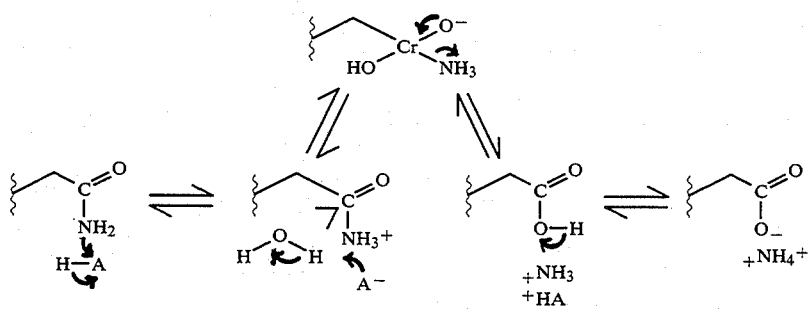

The general acid (HA) catalyzes the reaction by protonating the amido NH$_2$-leaving group of the ASN side chain. A general base can attack the carbonyl carbon of the amido group or activate another nucleophile by abstraction of a proton for attack on the amide carbon. Deamidation has been studied for a variety of specific proteins, a review of which is set forth in Wright, Critical Reviews in Biochemistry and Molecular Biology, 26:1 (1991), which is hereby incorporated by reference. These specific proteins include at least the following:
Aspartate aminotransferase
Calmodulin
Carbonic anhydrase (B, C)

Serine hydroxymethyltransferase
Somatotropin (human)
Substance P (human)
Acetylcholinesterase (cobra venom)
Amylase (human salivary)
Enterotoxin B (staphylococcus)
Phosphoryl carrier protein
Proteinass (alkaline)

It has been shown that the irreversible thermal denaturation of ribonuclease, lysozyme and α-amylase is controlled largely by the deamidation of Asn and Gln at acid and neutral pH and that a single deamidation in ribonuclease can affect folding kinetics. The observation that deamidation of Asn residues is a principle cause for the irreversible denaturation of proteins is an important aspect which implicates the role of Asn and Gln and the folding of proteins, their assembly into biologically active complexes, and their breakdown.

There are instances where one may wish to inactivate specific proteins using a deamidation process to promote unfolding of the target polypeptide. One example of such would be the selective disruption of a coat protein of a virus so as to prevent binding of the virus to its cellular receptor, thus preventing infection of the cell by the virus. Another example would be the disruption of the adhesion molecules on the surface of platelet cells, by which the platelets begin the process of blood clotting, in order to prevent clot formation. In such cases, it is clearly necessary to greatly accelerate the deamidation reaction. Catalysis of the reaction by an enzyme is a means of increasing the rate of deamidation under physiologically conditions.

The present invention, therefore, is focused on the discovery of an antibody which is capable of catalyzing a deamidation reaction, specifically the deamidation of an asparaginyl-glycyl dipeptide, which dipeptide may be contained in a larger polypeptide.

BRIEF DESCRIPTION OF THE DRAWINGS

FIG. 1 is a schematic drawing of an antibody protein.

FIG. 2 shows the overall reaction pathway of the deamidation of an asparginyl-glycyl dipeptide moiety to form aspartyl-glycyl dipeptide moiety or the isomerized backbone isoaspartyl-glycyl dipeptide moiety.

FIG. 3 shows the deamidation half of the overall reaction to form the ring-closed thalimide intermediate.

FIG. 4 shows the hydrolysis of the imide intermediate to form the final products of the deamidation reaction.

FIG. 5 shows the synthesis of the phospholane hapten used to raise the antibodies described in this application.

FIG. 6A and 6B show a general synthesis of a hapten containing a phospholane nucleus which is flanked by peptides so as to function as a hapten for raising antibodies specific for catalysis of the deamidation of a particular polypeptide containing an internal ASN-GLY dipeptide.

FIG. 7A and 7B shows the synthesis of a hapten containing a phospholane nucleus flanked by dipeptides so as to function as a hapten to elicit antibodies specific for catalysis of the deamidation of ASN 71 of human triosephosphate isomerase.

FIG. 8 schematically describes the assay used for quantitating the deamidation reaction.

FIG. 9A and 9B show the process for preparing the substrate utilized in the assay shown in FIG. 8.

FIGS. 10–12 are graphs of kinetic data for the antibodies.

FIG. 13 shows schematic diagrams of a set of λ vectors useful for producing Fab proteins from the entire antibody repertoire of a mammal from cDNA cloned from lymphoid tissue.

FIG. 14 shows the DNA sequences used to modify a λZAP vector DNA to produce the vectors of FIG. 13.

DETAILED DESCRIPTION OF THE INVENTION

As noted above, the fundamental aspect of the invention is the development of catalytic antibodies that would catalyze the ASN-GLY rearrangement or deamidation reaction. FIG. 2 sets forth the nature of the reaction which starts with a substrate 1 in which asparagine is joined through a peptide bond to glycine. The rearrangement is envisioned to go through the tetrahedral intermediate 2 and the initial product of the reaction is the ring-closed thalimide 3. The subsequent hydrolytic reaction occurs and forms two products 4 and 5, one including isoaspartic acid and the other including aspartic acid, so the net result is the deamidation of the asparagine to the aspartic acid or the rearrangement of the peptide chain to form the isoaspartic acid peptide. The present invention, therefore, is directed to a catalytic antibody that would carry out this reaction. The medical significance of this being that if one deamidates or one rearranges the original polypeptide backbone of a protein, there is biological evidence that proteins that have suffered such rearrangement or deamidation have lost catalytic activity in the case of enzymes or have lost biological properties, in the case of other receptor type proteins.

FIGS. 3 and 4 show the two steps of the deamidation reaction broken down into their respective tetrahedral intermediate and mechanistic properties.

FIG. 3 shows the deamidation reaction and also shows the actual model compound used in order to trace this process. The reaction forms a tetrahedral intermediate *2a* (shown before at 2 in the brackets in FIG. 2). FIG. 3 also shows the phosphonic acid derivative 6 which has a similar tetrahedral structure as intermediate *2a*, so that the phosphinic acid derivative 6 could be the hapten that would mimic this kind of intermediate. Thus, if one could indeed create this hapten, one would have a structure in the phosphoryl portion that would mimic the tetrahedral species of the intermediate transition compound *2a*.

The second part of the deamidation reaction is shown in FIG. 4 which is the hydrolysis of the resulting imide *4a*. That reaction can take two courses, hydroxide can attack the top carbonyl center of imide *4a* to make a tetrahedral intermediate *7a*, which then can give aspartic acid, or it can take the course of attack on the bottom carbonyl to make the tetrahedral intermediate *7b* and then isoaspartic acid when that tetrahedral intermediate *7b* reopens. As a result, choice of the hapten compound 6 initially permitted the construction of a tetrahedral intermediate for the cyclization which also has present a secondary hydroxyl function which mimics them, thereby allowing the hapten to mimic any of transition states *2a* or *7a* or *7b*. Thus, this is a first example of a hapten in which there is basically a design for two different types of transition states. This is believed to be the first such hapten which provides for the possibility of not only catalyzing the cyclization, but also the possibility of hydrolyzing the imide in an antibody catalytic reaction.

Having determined the structure of the hapten 6 of interest, FIG. 5 shows in schematic form a series of steps in which the basic structure, the phosphinic skeleton is put together by an arrangement of chemical steps. Above each arrow in FIG. 5 are the reagents and the conditions used to affect the given transformations. The procedure creates the hapten of choice, after deblocking in the last step, which can be then used (coupled to a protein) to produce a desired antibody.

Following preparation of the hapten, the hapten is then utilized to produce antibodies which being specific for the hapten will have corresponding specificity for the transition molecule mimicked by the hapten. Monoclonal antibodies can first of all be raised according to known procedures, such as those described by Kohler and Milstein (Nature 256:495 (1975)). Alternatively, Fab proteins can be produced which are designed to have binding specificity to the transition molecules. General procedures for the preparation of such Fabs are described in the literature at, for example, PCT International Publication No. W0 90/14430, hereby incorporated by reference.

Figure 2:
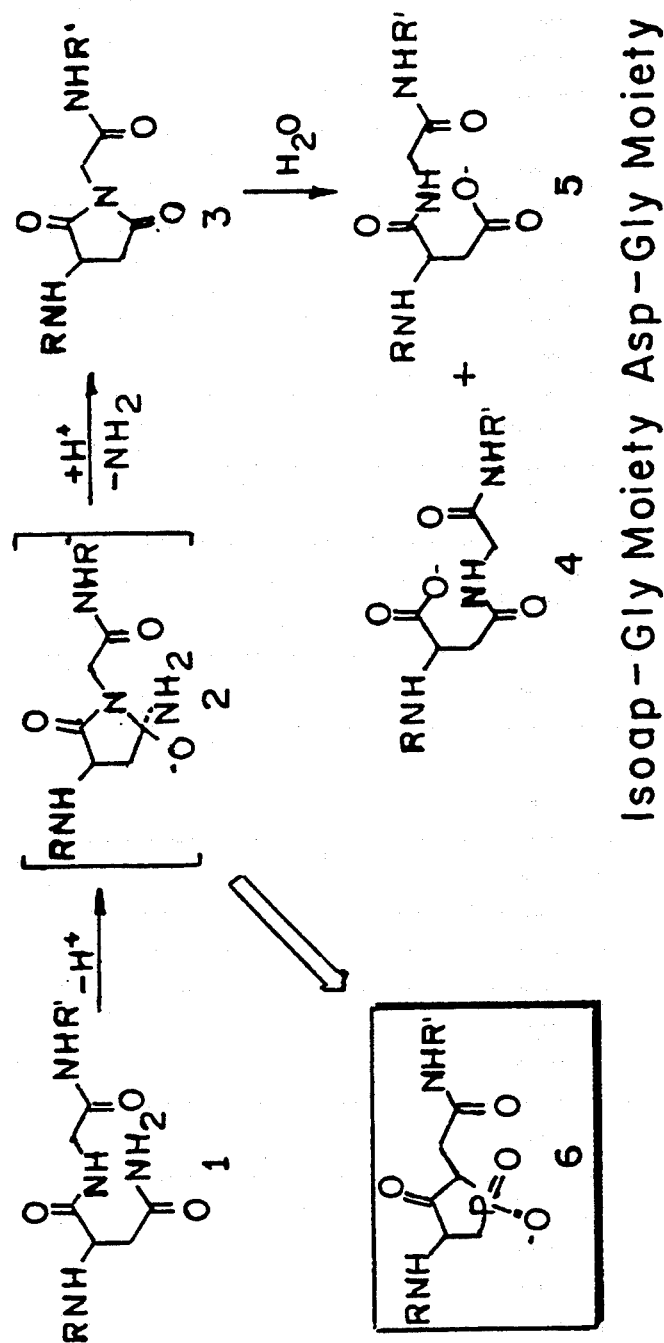

Procedure for preparation of the hapten 6-N-(2-phenylethyl )-[1'-hydroxyphosphol-3'-hydroxy-4'-(5-hydroxy-5-oxo-pentanoyl)amino-1'-oxo-2'-yl]acetamide disodium salt (RG2), a phospholane peptidomimetic hapten mimicking the transition state of the deamidation reaction:

The deamidation of an asparaginyl-glycyl dipeptide to form aspartyl-glycyl and isoaspartyl-glycyl dipeptide products is a two step reaction (FIGS. 2–4), composed of a nucleophilic attack upon the β-carbonyl of the asparagine residue by the peptide nitrogen to form the tetrahedral transition state (enclosed in brackets in FIG. 3) followed by loss of ammonia to form the imide intermediate. This intermediate is then hydrolyzed through a second tetrahedral intermediate (enclosed in brackets in FIG. 4) to form the two dipeptide products. N-(2-phenylethyl)-[1'-hydroxyphosphol-3'-hydroxy-4'-(5-hydroxy-5-oxo-pentanoyl) amino-1'-oxo-2'-yl[acetamide (RG2) is a compound which mimics both the tetrahedral transition state of the ring closing deamidation and the tetrahedral transition state of the hydrolysis step.

Figure 5:
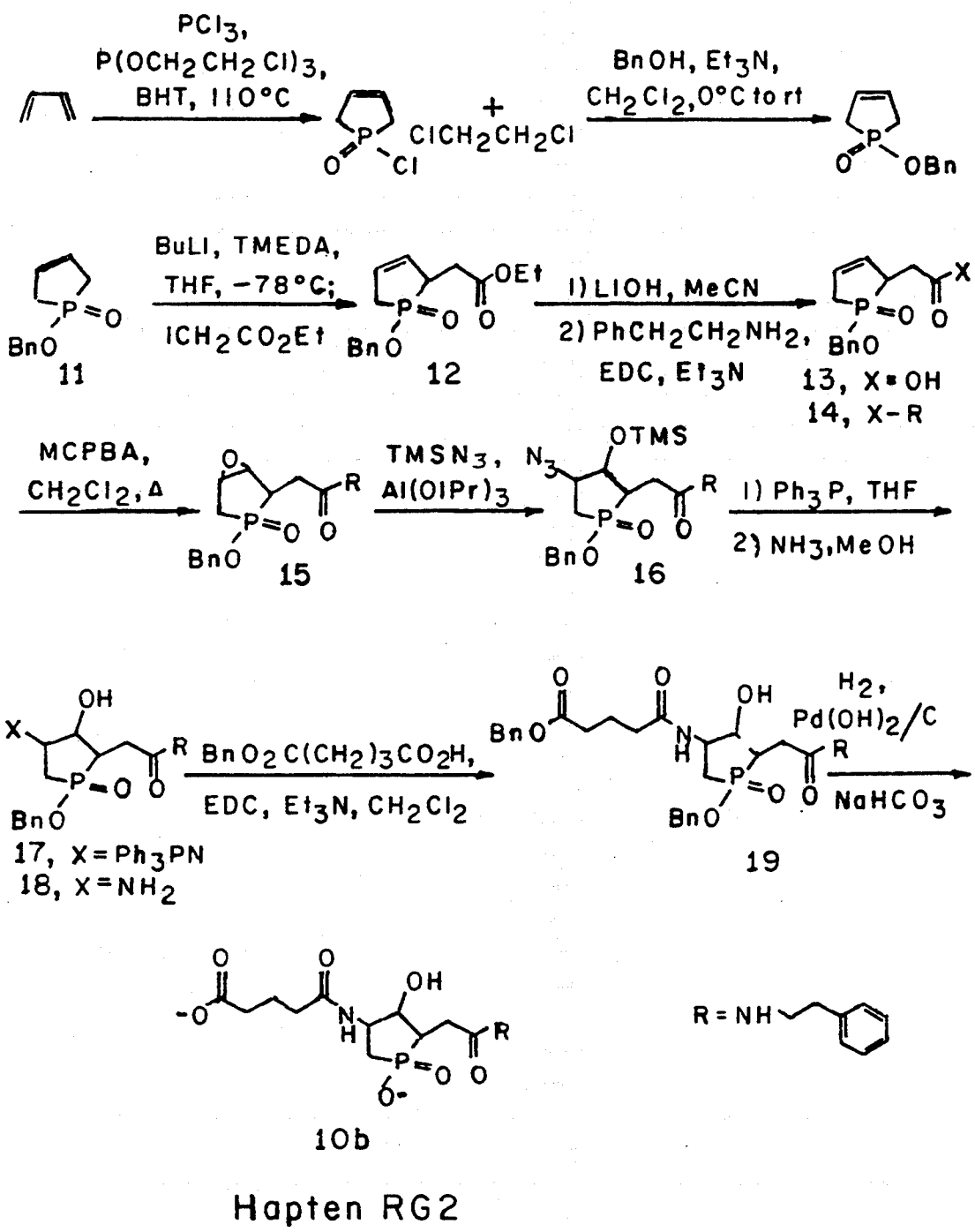

Preparation of the RG2 hapten is shown in FIG. 5 and begins with synthesis of 1-Benzyloxyphosphol-3-ene-1-oxide (intermediate 11). A thick walled glass tube (Ace Glass Co., Catalog number 8648-83, ~120 mL capacity) equipped with a stirbar is cooled to ~ −30° C. and charged with $PCl_3$(17.5 mL, 27.5 g, 0.20 mol), $P(OCH_2CH_2Cl)_3$ (20.3 mL, 27.0 g, 0.10 mol), 2,6-di-tert-butyl-p-cresol (0.22 g, 0.001 mol), and liquid butadiene (condensed from gaseous $C_4H_6$ at −70 C; 27 mL, 17 g, 0.32 mol). The glass tube is then sealed with a screw cap and heated to 105° C. using an oil bath. After 19h, the tube is removed from the oil bath and allowed to cool to room temperature. Filtration of the cloudy yellow solution affords a mixture of 1,2-dichloroethane and the desired 1-chlorophosphol-3-ene-1-oxide along with a small amount of the 1-hydroxyphosphol-3-ene-1-oxide. $^1$H-NMR (360 MHz, CDCl$_3$) ∂6.0 (d, $J_{H-P}$~33 Hz, 2H) , 3.7 (s, 4H, ClCH$_2$CH$_2$Cl), 3.1–2.8 (m, 4H); $^{13}$C-NMR (90 MHz, CDCl$_3$) ∂126.2 (d, $J_{C-P}$~17 Hz), 36.5 (d, $J_{C-P}$~76 Hz); $^{31}$P-NMR (90 MHz, CDCl$_3$) ∂80.9.

To a rapidly stirred solution of PhCH$_2$OH (4.6 mL, 44.3 mmol) in Et$_3$N (20 mL) and CH$_2$Cl$_2$ (45 mL) at 0° C. is added a portion of the crude phospholene/1,2-dichloroethane mixture (∂40 mmol) dropwise slowly via syringe. The resulting suspension is stirred for 12 h at room temperature, concentrated (rotovap), and the resulting white solid is taken up in CH$_2$Cl$_2$ (∂200 mL). The solution is then washed with saturated aqueous NaHCO$_3$ (3×50 mL), dried (MgSO$_4$), filtered and concentrated. Purification by flash chromatography (5×15 cm silica gel, 80% EtOAc/hexanes) affords 6.8 g (81%) of the desired benzyl-protected product (compound 11) as a pale yellow oil: $^1$H-NMR (360 MHz, CDCl$_3$) ∂7.5–7.3 (m, 5H), 5.9 (d, $J_{H-P}$∂33.4 Hz, 2H), 5.1 (d, $J_{H-P}$∂78.8 Hz, 2H), 3.0–2.8 (m, 4H); $^{13}$C-NMR (90 MHz, CDCl$_3$) ∂136.2, 128.7, 128.5, 128.0, 127.0, 126.8, 66.3 (d, $J_{C-P}$∂5 Hz), 29.4 (d, $J_{C-P}$∂91 Hz); $^{31}$P-NMR (90 MHz, CDCl$_3$) ∂73.9; EI mass spectrum m/z (relative intensity) 208 (23) , 102 (25) , 91 (100), 65 (16); HRMS 208.0654 (calculated from C$_{11}$H$_{13}$PO$_2$: 208.0653) .

Ethyl (1'-Benzyloxyphosphol-3'-ene-1'-oxo-2'-yl)acetate (compound 12). To a rapidly stirred solution of benzyl phosphinate (intermediate 11) (416 mg, 2.0 mmol) in N,N,N'N' tetramethylethylene diamine (TMEDA, 1.5 mL) and tetrahydrofuran (THF, distilled from Na/benzophenone ketyl; 2.5 mL) at −70° C. under argon (Ar) is added n-butyl lithium (nBuLi, 2.5M in hexanes, 0.96 mL, 2.4 mmol) dropwise slowly via syringe. The orange-red solution is stirred for 30 min. and then ethyl iodoacetate (0.36 mL, 3.0 mmol) is added neat via syringe. The resulting suspension is warmed to ~ −10° C. quenched with 25 mL saturated NH$_4$Cl and extracted with CHCl$_3$ (3×50 mL). The combined organic layers are then dried (MgSO$_4$), filtered and concentrated. Purification by flash chromatography (3×15 cm silica gel, 80% EtOAc/hexanes) affords 125 mg (21%) of intermediate 12, as a yellow oil: $^1$H-NMR (360 MHz, CDCl$_3$) ∂7.5–7.2 (m, 5H), 6.0–5.8 (m, 2H), 5.2–5.1 (m, 2H), 4.15 (q, J~7 Hz, 2H), 2.9 (m, 1H), 2.75 (m, 1H), 2.5–2.3 (m, 3H), 1.25 (t, J~7 Hz, 3H); $^{13}$C-NMR (909 MHz, CDCl$_3$) ∂171.8 (d, $J_{C-P}$~9 Hz), 136.3 (d, $J_{C-P}$~7 Hz) , 131.5 (d, $J_{C-P}$~ 19 Hz), 128.5, 128.3, 127.9, 126.4 (d, $J_{C-P}$~ 15 Hz) , 66.5 (d, $J_{C-P}$7 Hz) , 60.7, 35.4 (d, $J_{C-P}$~92 Hz), 33.4, 29.7 (d, $J_{C-P}$92 Hz) 14.1; −P-NMR (90 MHz, CDCl$_3$) ∂71.3; EI mass spectrum m/z (relative intensity) 294 (4), 208 (10), 102 (13), 91 (100), 65 (10); HRMS 294.1029 (calculated for C$_{15}$H$_{19}$PO$_4$: 294.1021).

N-(2-Phenylethyl)-(1'-Benzyloxyphosphol-3'-ene-1'-oxo-2'-yl ) acetamide (intermediate 14). To a well stirred solution of ethyl ester (intermediate 12) (524 mg, 1.78 mmol) in CH$_3$CN (12.0 mL) is added LiOH (0.25M, 7.12 mL, 1.78 mmol) dropwise via a syringe. After 1 h at room temperature, the reaction is quenched by addition of 1M HCl to a final pH of ~3. The resulting suspension is extracted with CHCl$_3$(3×50 mL) and the combined organic layers are then dried (MgSO$_4$), filtered and concentrated. Purification by flash chromatography (2×15 cm silica gel, 10% MeOH/CHCl$_3$) affords 300 mg (66%) of (1'-benzyloxyphosphol-3'ene-1'-oxo-2'-yl) acetic acid (intermediate 13): $^1$H-NMR (360MHZ, CDCl$_3$) ∂7.5–7.2 (m, 5H), 6.0–5.7 (m, 2H), 5.2 (m, 2H), 3.0 (m, 1H), 2.8–2.3 (m, 4H); $^{31}$P-NMR (90MHz, CDCl$_3$) ∂74.3; CI mass spectrum m/z (relative intensity) 267 (30, MH+), 199 (5), 159 (100), 91 (37). To a solution of the acid (300 rag, 1.13 mmol) in CH$_2$Cl$_2$ (10 mL) is added Et$_3$N (0.31 mL, 2.26 mmol), phenethylamine (0.28 mL, 2.26 mmol), and EDC (1-(3-dimethylaminopropyl)-3-ethylcarbodiimide hydrochloride; 258 mg, 1.35 mmol). The resulting solution is stirred from 48 h at room temperature, and then taken up in additional CH$_2$Cl$_2$ (~50 mL). The organic layer is then washed with 1N aqueous HCl (4×20 mL), dried (MgSO$_4$), filtered and concentrated. Purification by flash chromatography (2×15 cm silica gel, EtOAc) affords 107 mg (26%) of the desired amide (intermediate 14) as a yellowgreen solid: $^1$H-NMR (360MHz, CDCl$_3$) ∂7.5–7.1 (m, 10H), 6.5 (br s, 1H), 6.0–5.7 (m, 2H), 5.2–5.0 (m, 2H), 3.7–3.4 (m, 2H), 3.0 (m, 1H), 2.85 (t, J~7Hz, 2H), 2.6 (m, 1H), 2.5–2.3 (m, 3H); $^{13}$C-NMR (90MHz, CDCl$_3$) ∂170.6 (d, $J_{C-P}$~7Hz) , 138.8, 136.5, 136.1, 132.2 (d, $J_{C-P}$~20 Hz) , 128.7, 128.6, 128.55, 128.5, 128.0, 126.4, 126.0 (d, $J_{C-P}$~90 Hz); $^{31}$P-NMR (90MHz, CDCl$_3$) ∂73.1; LR mass spectrum m/z (relative intensity) 369 (11) , 249 (12) , 105 (11) , 104 (15), 91

(base); HRMS 369.1467 (calculated for $C_{21}H_{24}NO_3P$; 369.1494).

N-(2-Phenylethyl)-(1'-Benzyloxyphosphol-3',4'-epoxy-1'-oxo-2'-yl)acetamide (intermediate 15). A solution of amide (intermediate 14) (227 mg, 0.615 mmol) and m-chloroperbenzoic acid (72%, 206 mg, 0.86 mmol) in $CH_2Cl_2$ (2.5 mL) is refluxed under Ar for 24 h, stirred for 12 h at room temperature, and then stirred for 1 h with saturated aqueous $NaHCO_3$ (~2.5 mL). The mixture is then taken up in $CH_2Cl_2$ (~100 mL) and washed with saturated $NaHCO_3$ (3×25 mL) and the combined aqueous layers are back-extracted with $CH_2Cl_2$ (1×25 mL). The combined organic layers are then dried ($MgSO_4$), filtered and concentrated. Purification by flash chromatography (2×15 cm silica gel, 3% $MeOH/CHCl_3$) affords 136 mg (57%) of epoxide (intermediate 15). $^1$H-NMR (360MHz, $CDCl_3$) $\partial$7.5–7.1 (m, 10H), 6.9 (br s, 1H), 5.1–5.0 (m, 2H), 3.7–3.4 (m, 4H), 3.0–2.8 (m, 1H), 2.85 (t, J~7 Hz, 2H), 2.7–2.5 (m, 2H), 2.2–2.0 (m, 2H); $^{13}$C-NMR (90MHz, $CDCl_3$) $\partial$170.5 (d, $J_{C-P}$~10.5 Hz), 138.9, 135.9, 128.6, 128.56, 128.5, 128.4, 128.1, 126.2, 66.5 (d, $J_{C-P}$~6.5 Hz), 57.4 (d, $J_{C-P}$~10.5 Hz), 52.4 (d, $J_{C-P}$~5 Hz), 40.7, 35.5, 34.7 (d, $J_{C-P}$~90 Hz), 31.7, 28.8 (d, $J_{C-P}$~90 Hz); $^{31}$P-NMR (90MHz, $CDCl_3$) $\partial$70.8; LR mass spectrum m/z (relative intensity) 385 (5), 294 (5), 265 (9), 120 (7), 104 (11), 91 (100), 65 (5); HRMS x (calculated for $C_{21}H_{24}NO_4P$: x) .

N-(2-Phenylethyl)-(1'-Benzyloxyphosphol-3'-trimethylsiloxy-4'-azido-1'-oxo-2'-yl) acetamide (intermediate 16). Azidotrimethylsilane ($TMSN_3$, 0.14 mL, 1.06 mmol), aluminum isopropoxide (Al $(OiPr)_3$, 22 mg, 0.11 mmol) and $CH_2Cl_2$ (2.5 mL) are stirred together under Ar for 2 h at room temperature. Epoxide (intermediate 15) (136 mg, 0.353 mmol) is dissolved in $CH_2Cl_2$ (1 mL + 1 mL washing) and added via cannula. After 3 days, the mixture is taken up in $CH_2Cl_2$ (~50 mL) and filtered through celite. The solvent is then removed and the crude oil purified by flash chromatography (2×15 cm silica gel, EtOAc) to afford 70 mg (40%) of azide (intermediate 16): $^1$H-NMR (360MHz, $CDCl_3$) $\partial$7.5–7.1 (m, 10H), 6.4–6.3 (m, 1H), 5.1–5.0 (m, 2H), 4.2–3.4 (m, 4H), 2.85 (t, J~7 Hz, 2H), 2.8–2.1 (m, 4H), 1.9–1.7 (m, 1H), 0.1 (s, 9H); $^{13}$C-NMR (90MHz, $CDCl_3$) $\partial$; $^{31}$P-NMR (90MHz, $CDCl_3$) $\partial$66.8, 56.1; LR mass spectrum m/z (relative intensity) 500 (5), 409 (6), 380 (9), 120 (6), 105 (13), 104 (13), 91 (100), 73 (14); HRMS 500.1965 (calculated for $C_{24}H_{33}N_4O_4PSi$: 500.2009).

N-(2-Phenylethyl)-(1'-Benzyloxyphosphol-3'-hydroxy-4'-amino-1'-oxo-2'-yl)acetamide (intermediate 18). Azide (intermediate 16) (70 mg, 0.14 mmol) and water (7.6 μL, 0.42 mmol) are dissolved in tetrahydrofuran (1.2 mL). Triphenylphosphine (73 mg, 0.28 mmol) is added and the reaction is stirred ~14 h at room temperature. The mixture is then concentrated and purified by flash chromatography (2×15 cm silica gel, 20% $MeOH/CHCl_3$) to afford ~100 mg (~100%) of N-(2-phenylethyl)-(1'-benzyloxyphosphol-3'-hydroxy-4'-triphenylphosphazin-1'-oxo-2'-yl)acetamide (intermediate 17): Positive ion FAB mass spectrum: 663. A solution of intermediate 17 (~100 mg) in MeOH (15 mL) is cooled to 0° C. and saturated with gaseous $NH_3$. The stoppered flask is then allowed to come to room temperature. After 20 h, the solvent is removed and the residue chromatographed (2×15 cm silica gel, 30% $MeOH/CHCl_3$) to afford 30 mg (53%) of the desired amine (intermediate 18): $^1$H-NMR (360MHz, $CDCl_3$) $\partial$7.4–7.1 (m, 10H), 7.1–6.9 (m, 1H), 5.1–4.9 (m, 2H), 4.0–3.7 (m, 1H), 3.6–3.2 (m, 5H), 2.85 (t, J~7 Hz, 2H), 2.72.–2.1(m, 5H), 1.9–1.5 (m, 1H); $^{13}$C-NMR (90MHz, $CDCl_3$) $\partial$; $^{31}$P-NMR (90MHz, $CDCl_3$) $\partial$70.2, 61.5; Positive ion FAB mass spectrum: 403 (MH+).

N-(2-Phenylethyl)-[1'-Benzyloxyphosphol-3'-hydroxy-4'-(5-benzyloxy-5-oxo-pentanoyl)amino-1'-oxo-2'-yl]acetamide (product 19). A solution of amine (intermediate 18) (30 mg, 0,075 mmol), monobenzyl glutarate (20 mg, 0.090 mmol), $Et_3N$ (15.6 μL, 0.11 mmol), and EDC (17.0 mg, 0.090 mmol) in $CH_2Cl_2$ (3.0 mL) is stirred for 48 h at room temperature. The reaction mixture is then concentrated and purified by flash chromatography (2×15 cm silica gel, 5% $MeOH/CHCl_3$) to afford 25 mg (55%) of the desired amide (product 19): $^1$HNMR (360MHz, $CDCl_3$) $\partial$; $^{13}$C-NMR (90MHz, $CDCl_3$) $\partial$; $^{31}$P-NMR (90 MHz, $CDCl_3$) $\partial$69.5, 58.7; Positive ion FAB mass spectrum: 607 (MH+).

N-(Z-Phenylethyl)-[1'-hydroxyphosphol-3'-hydroxy-4'-(5-hydroxy-5-oxo-pentanoyl)amino-1'-oxo-2'-yl]acetamide disodium salt (product 10b, RG2). A solution of dibenzylprotected protected hapten (intermediate 19) (25 mg, 0.041 mmol), $NaHCO_3$ (0.5M in $H_2O$, 83 μL, 0,083 mmol), $Pd(OH)_2/C$ (~10 mg), in EtOH (~10 mL) is stirred under $H_2$ for 16 h at room temperature and atmospheric pressure. The reaction mixture is then filtered through a plug of celite and glass wool and concentrated to afford 20 mg (100%) of the hapten (10b): $^1$H-NMR (360MHz, $CD_3OD$) $\partial$7.4–7.1 (m, 5H), 4.2–3.7 (m, 2H), 3.5–3.2 (m, 2H), 2.8 (t, J~7 Hz, 2H), 2.6–1.9 (m, 10H), 1.7–1.4 (m, 1H); $^{13}$C-NMR (90MHz, $CDCl_3$) $\partial$; $^{31}$P-NMR (90 MHz, $CDCl_3$) $\partial$69.5, 58.7.

The thus produced hapten RG2 has the following structure of formula (I)

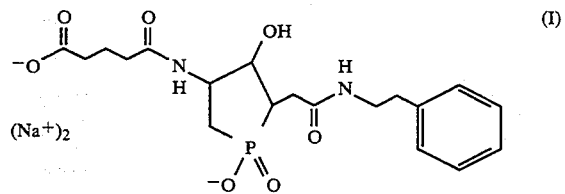

Figure 3:
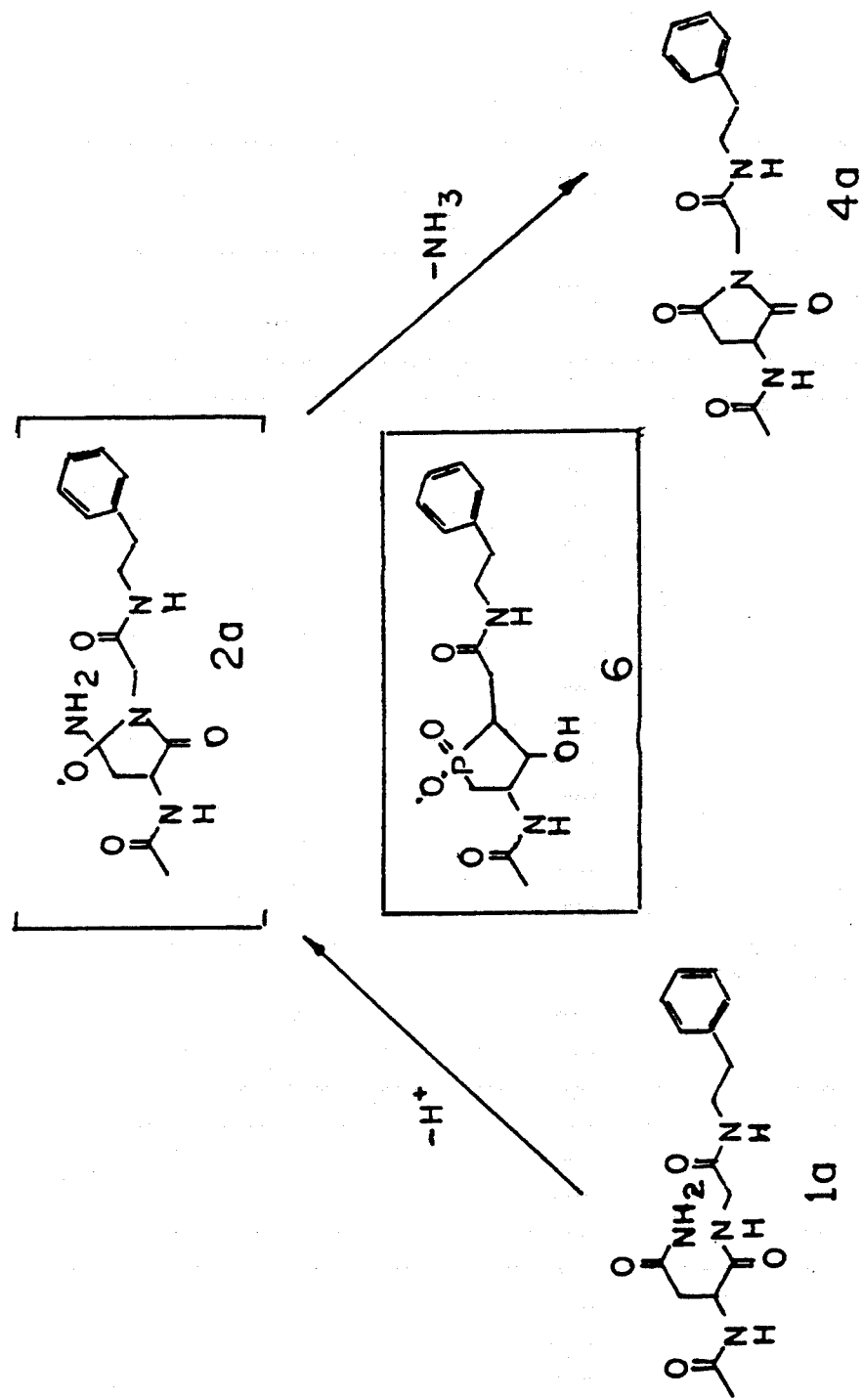
Figure 4:
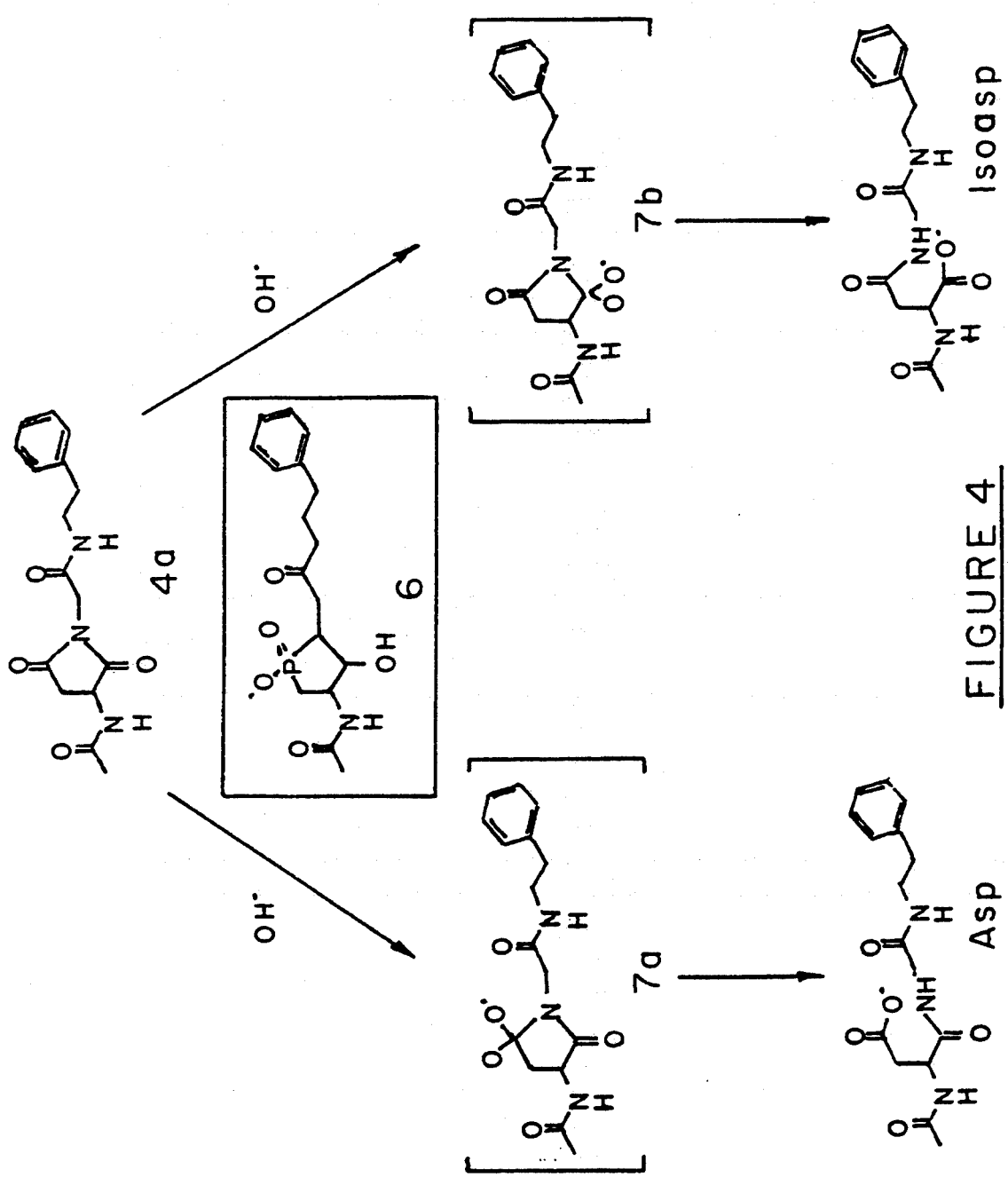

This hapten, as discussed above, has a structure which mimics that of the important transition state of the deamidation reaction as can be best seen in FIG. 3 by a comparison of the hapten 6 with the transition state 2a and, therefore, is the target hapten for preparation of the desired catalytic antibodies.

Syntheses of the RG2 hapten (hapten 6, formula (I)), modified so as to replace one or both of the oxygen atoms attached to the phosphorous, or to introduce a thiol for the hydroxy substituent of the five-membered ring, are considered to fall within the scope of the hapten invention. Such variants are likely to have a three-dimensional structure similar to that of the RG2 hapten and thus would be expected to function to elicit antibodies that catalyze ASN-GLY deamidation. This hypothesis could be confirmed by synthesizing such variants and assaying them for activity as competitive inhibitors of antibodies elicited by the RG2 hapten in the ASN-GLY deamidation reaction.

As a result, a broader aspect of the present invention is directed to a molecule (hapten) consisting of a molecule having a three-dimensional structure sufficiently similar to the three-dimensional structure of the RG2 hapten so as to function as a competitive inhibitor of the binding of the RG2 hapten to a molecule (such as an antibody) which binds the RG2 hapten. Such a compound can be represented by the following formula

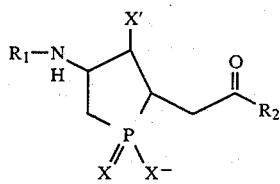

wherein $R_1$ and $R_2$ are moieties selected from the group consisting of a primary amine, a secondary amine, a tertiary amine, a substituted methylene, an N-substituted $\beta$-carboxyamide, an amino acid residue and a peptide residue, and X' is =O, =S or —OH, or a salt thereof. Preferred among this group of compounds are those of the formula:

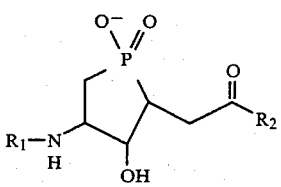

wherein $R_1$ and $R_2$ are each the residue of at least one amino acid, or a salt thereof.

Procedure for Preparation of Antibodies Catalyzing Deamidation of a Specific Protein:

The phospholane peptidomimetic hapten RG2 (product 10b) described above is useful in eliciting antibodies which catalyze the deamidation of asparaginyl-glycyl dipeptides indiscriminately. However, in order to direct the catalytic proteins to deamidate a specific polypeptide target, it is necessary to increase the size of the hapten to show a larger, more specific epitope. This can be accomplished by attaching oligopeptide chains on either side of the phospholane nucleus of the hapten which duplicate the amino acid sequence surrounding the asparaginyl-glycyl dipeptide in the target protein. As a result, the hapten of the invention can be utilized to produce a catalytic antibody for catalyzing the deamidation of Asn-Gly in virtually any target protein by taking advantage of the hapten structure for catalytic purposes and taking advantage of the structure of the selected protein to selectively catalyze deamidation of particularly the selected protein.

Thus, to produce a catalytic antibody directed to a selected protein of interest, the following design scheme is followed.

(1) The target protein of interest is selected and its amino acid sequence determined, or at least a portion of its sequence encompassing at least about two to seven amino acids on either side of an Asn-Gly linkage.

(2) A first oligopeptide is produced which has the structure of about two to seven amino acids upstream from the Asn-Gly linkage, and a second oligopeptide is produced which has the structure of about two to seven amino acids downstream of the Asn-Gly linkage.

(3) The hapten RG2 is then prepared such that the thus synthesized first and second oligopeptides are attached on either side of the phospholane nucleus as shown below:

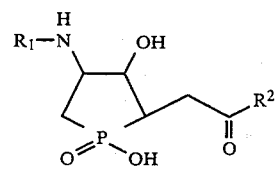

wherein $R^1$ and $R^2$ comprise the first and second oligopeptides.

(4) The thus produced product, if desired, is coupled to an appropriate carrier molecule (such as BSA or KLH) to stimulate an antigenic response.

(5) The thus produced antigenic molecule is utilized to produce monoclonal antibodies.

(6) The monoclonal antibodies thus produced are then assayed to select those having the desired catalytic activity.

Figure 6A:
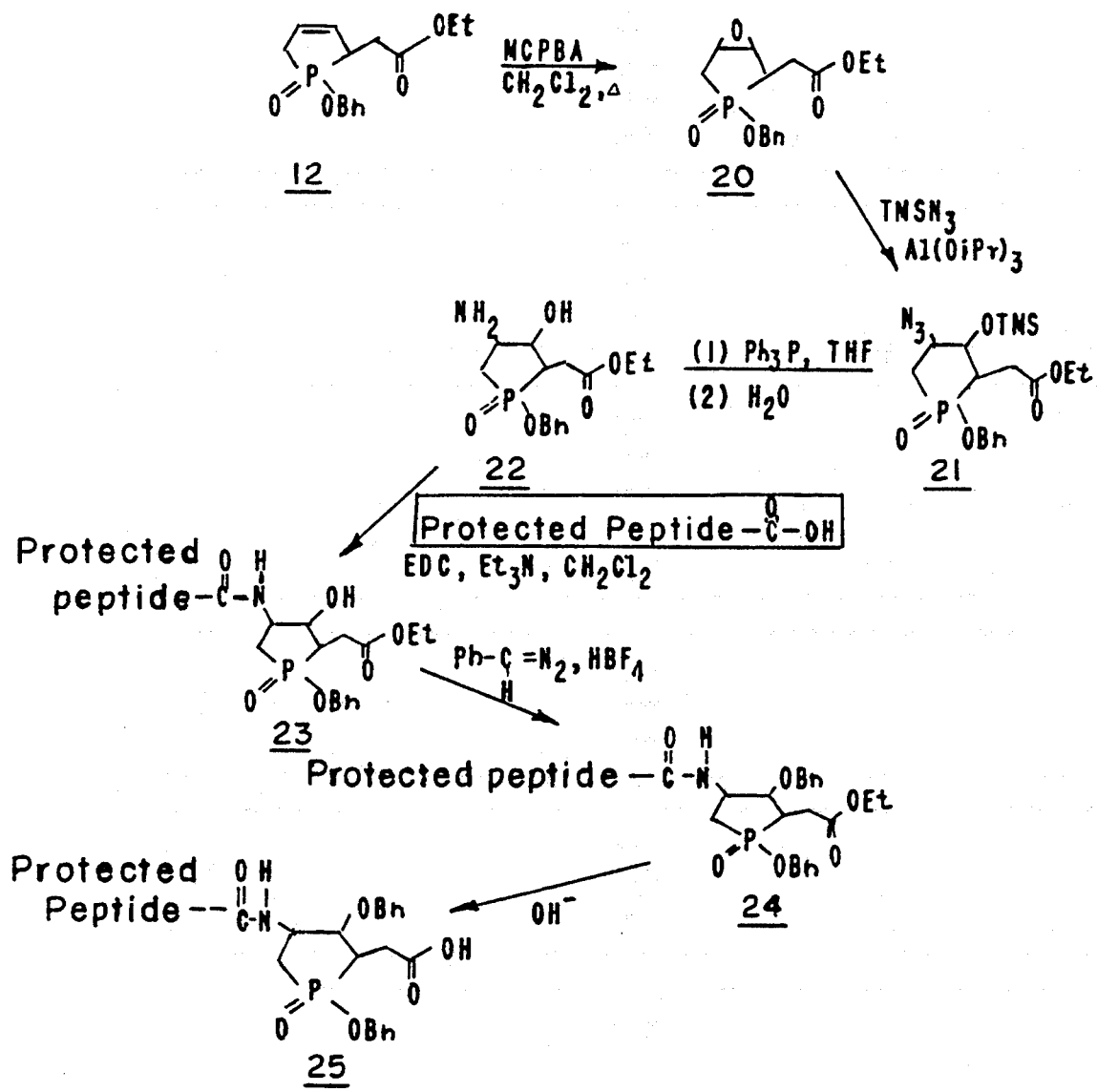
Figure 6B:
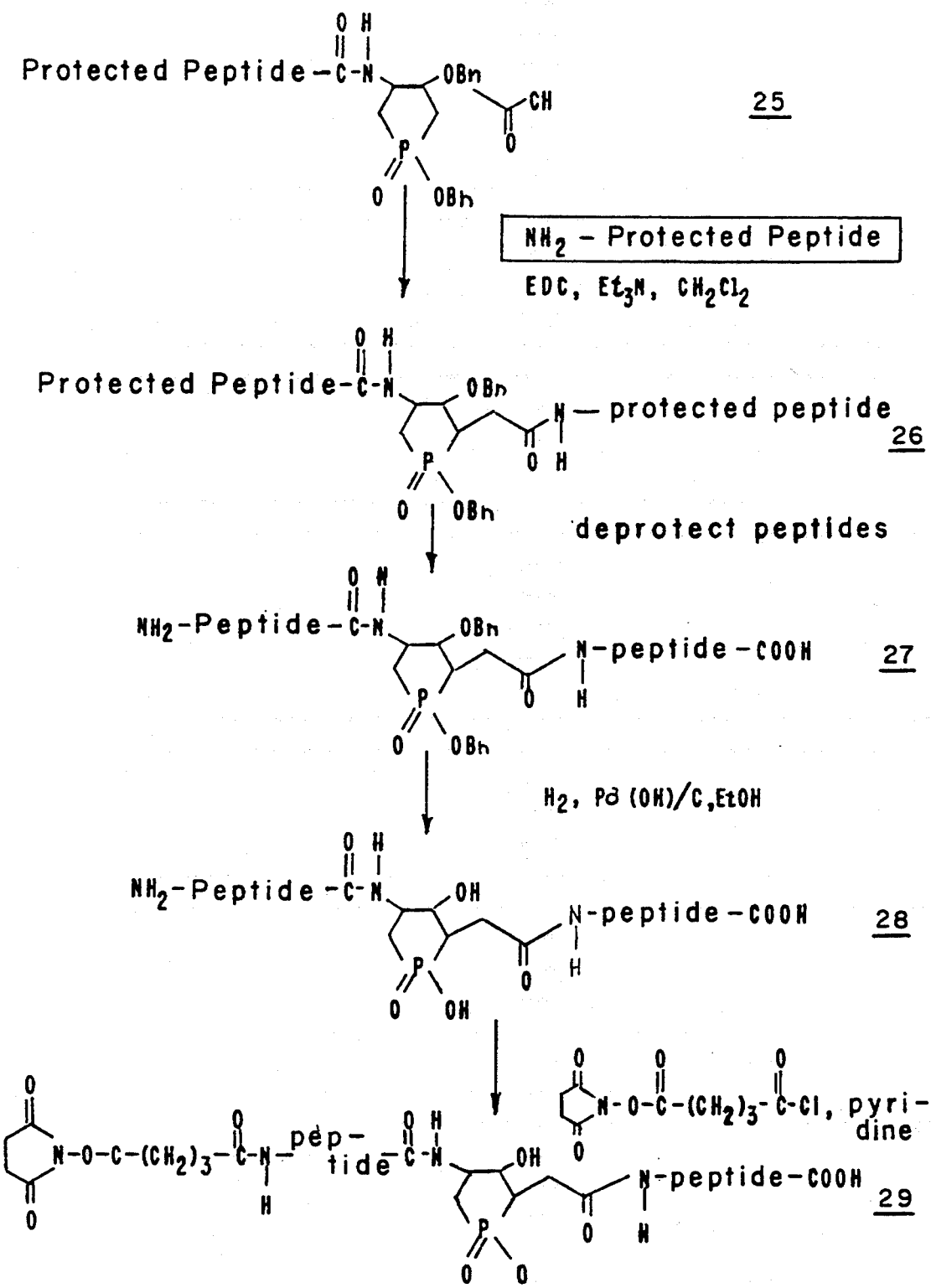

More specifically, the procedure for preparing the hapten for a selected target protein can follow the Scheme set forth in FIGS. 6a and 6b.

Figure 7A:
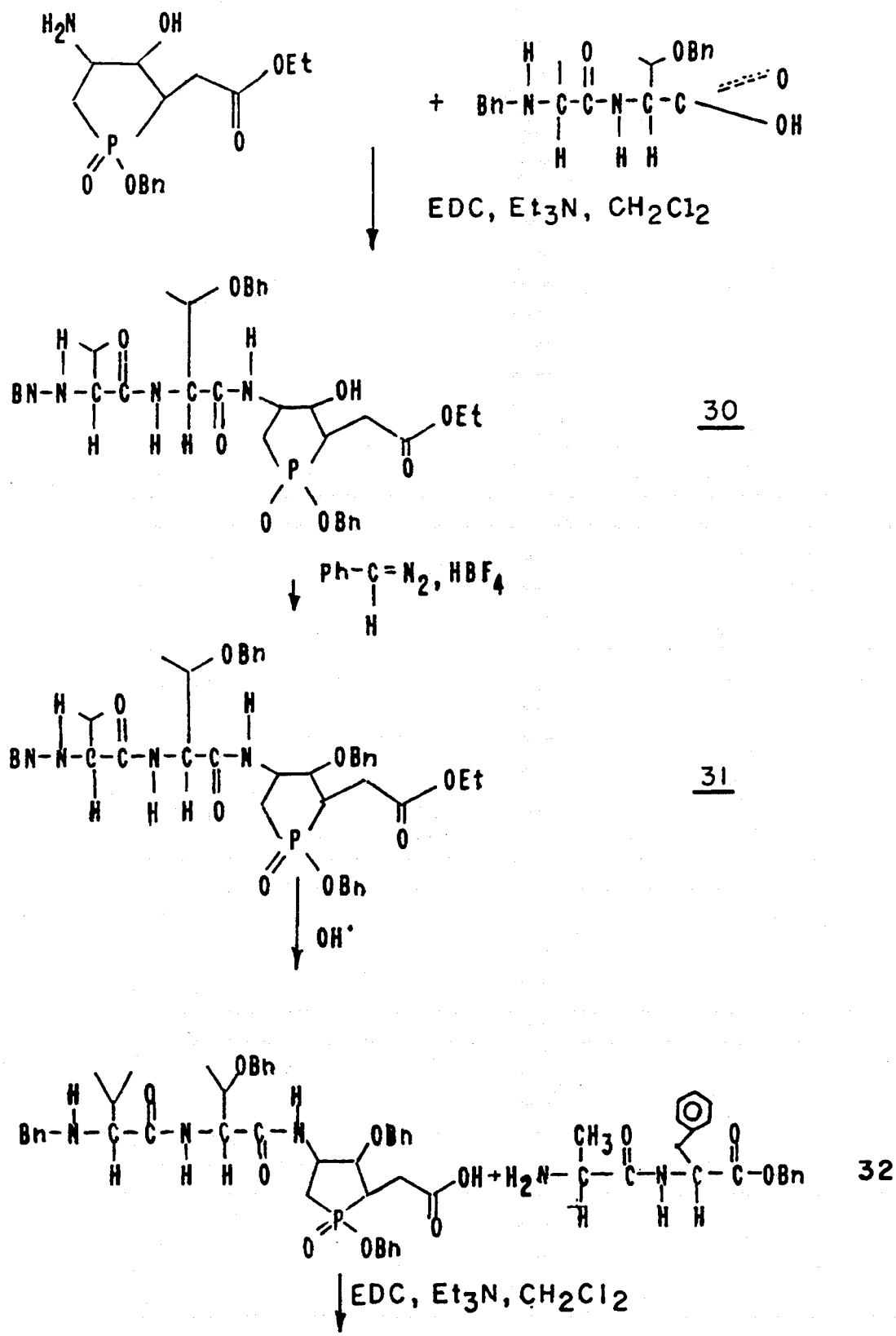
Figure 7B:
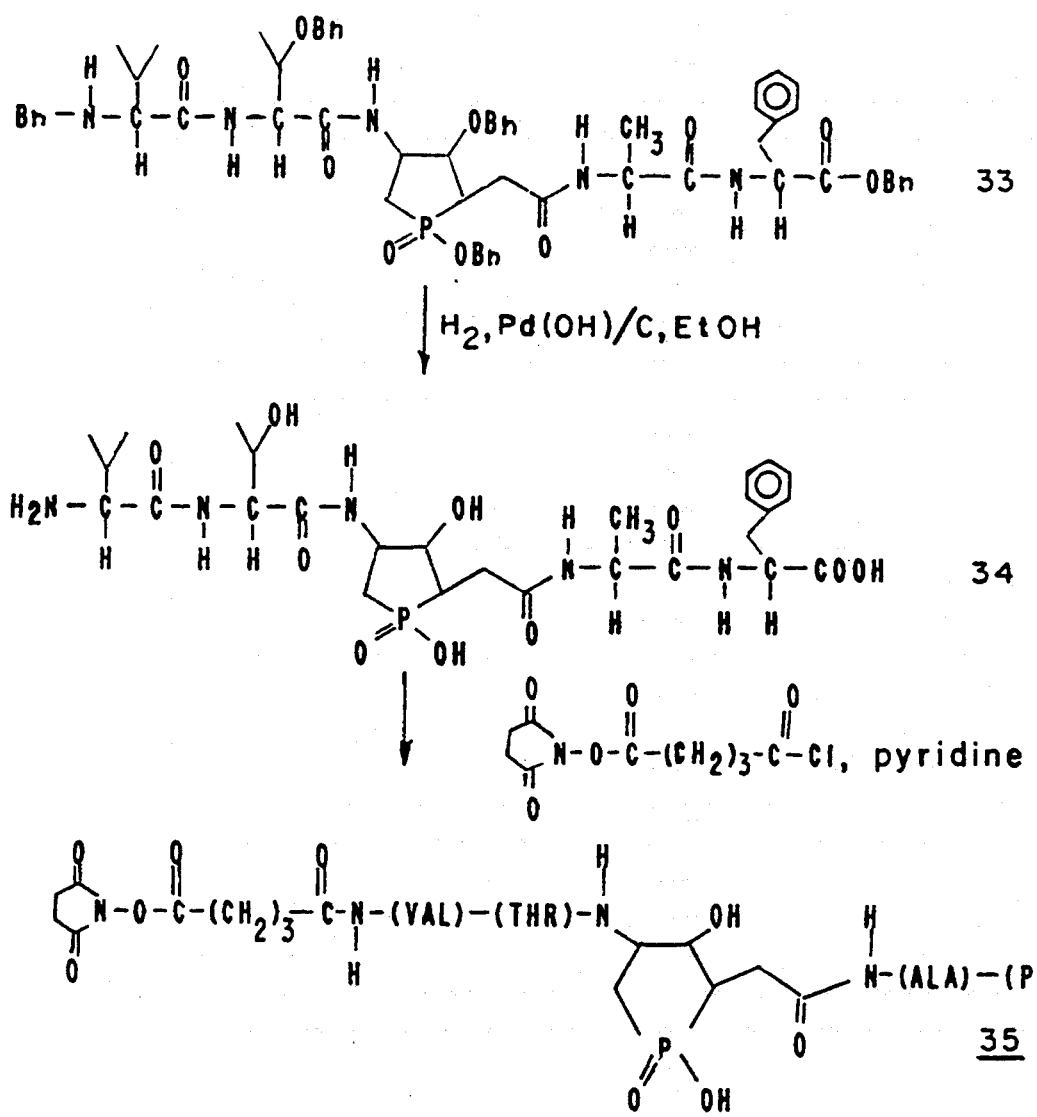

This Scheme shows the general procedure for synthesis of a hapten for the production of catalytic antibodies for the deamidation of any specific protein; while the synthesis of a hapten for the deamidation of a particular protein, human triose phosphate isomerase, is shown in FIG. 7. In FIGS. 6a and 6b, the $R^1$ and $R^2$ groups of formula (II) above are denoted as "protected peptides". This nomenclature is chosen because the protecting groups used will depend upon the specifics of the peptides which are chosen to be appended to the phospholane nucleus. The particulars of the protecting groups would be obvious to one skilled in peptide chemistry as protecting groups well known in the art can be utilized. The following abbreviations are used in the reaction schemes:

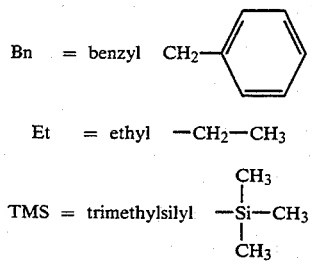

The structure of the RG2 hapten may be modified so that it may be used to induce antibodies that will catalyze the deamidation and isomerization (isomerization to yield α-linked or β-linked ASP-GLY sequence) of any peptide or protein containing an ASN-GLY sequence. Such a modification will only require the attachment of those amino acids that flank the ASN-GLY sequence in the peptide or protein to the cyclic phosphinate ring of the hapten. A description of a general synthesis of such a hapten is described below and shown in FIGS. 6a and 6b.

Epoxidation of compound 12 (synthesized as described above and shown in FIG. 5) to form compound 20 is achieved using meta-chloroperbenzoic acid (MCPBA) in methylene chloride. Compound 20 is converted to compound 21 using azidotrimethyl silane and aluminum isopropoxide. Compound 21 is converted into 22 using triphenylphosphine and water in THF. The amino group of compound 22 may be coupled to the carboxyl terminus of any suitably protected amino acid (the amino terminus is protected as well as any functional groups on the amino acid side chains), peptide or protein using EDC (1-(3-dimethylaminopropyl)-3-ethyl carbodiimide) and triethylamine (Et$_3$N) in methylene chloride to give coinpounds of general structure 23. Protection of the hydroxyl group of 23 with phenyldiazomethane and fluoroboric acid yields compound 24. Compound 24 is converted into the carboxylic acid derivative, 25, in aqueous base which can then be coupled to the amino terminus of any suitably protected amino acid, peptide or protein (the protecting groups used on the amino acids will depend upon which amino acids are used) using EDC and triethylamine yielding compounds of general structure 26. The peptides are then deprotected to give compound 27 (the conditions for the deprotection of the amino acids/peptides or proteins attached to the cyclic phosphinate will depend upon which amino acids are used). Reaction of 27 with hydrogen and palladium hydroxide over carbon in ethanol yields 28 with the unprotected amino acids, peptides or proteins attached to the cyclic phosphinate nucleus. The amino terminus of one of the peptide chains is then reacted with succinimidyl hemiglutarylchloride in pyridine to give the hapten 29. This can be coupled to the carrier protein, such as keyhole limpet hemocyanin. This carrier protein-hapten conjugate can then be used to induce antibodies that will be assayed for their ability to deamidate and isomerize an ASN-GLY containing peptide or protein.

A specific example of how a hapten may be constructed that will induce antibodies to deamidate and isomerize the enzyme triosephosphate isomerase from human placenta is described below.

Example 1

Preparation of a Hapten Used to Raise an Antibody to Catalyze Deamidation of Triosephosphate Isomerase:

Triosephosphate isomerase (from human placenta) contains several ASN-GLY sequences. The ASN-GLY sequence at ASN 71 is flanked by valine, threonine, alanine and phenylalanine (Lu et al, J. Bio. Chem., 259, 1958, (1984)) as shown below:

PROTEIN-NH-VAL-THR-ASN-GLY-ALA-PHE-CO-PROTEIN

E.,PROTEIN-8Cl ID NO:1-PROTEIN).

In order to generate an antibody that will recognize and deamidate the ASN and isomerize the protein at the ASN-GLY dipeptide within the specific sequence above, a cyclic phosphinate hapten must be constructed that has those flanking amino acids attached to it. Thus a VAL-THR dipeptide must be attached to the amino group of compound 22 of FIG. 6a and an ALA-PHE dipeptide must be attached to the carboxyl group of a compound similar to 25 of FIG. 6a. The synthesis of such a compound, starting from compound 22 is described below and shown in FIG. 7.

Compound 22 (prepared as described above) is coupled with the carboxyl terminus of a VAL-THR dipeptide (which has been protected with a benzyl group at both the amino terminus and the hydroxyl group of the threonine side chain) using EDC and triethylamine to give compound 30. Reaction of compound 30 with phenyl diazomethane and fluoroboric acid yields compound 31. Hydrolysis of the ester group in 31 with aqueous base yields compound 32. Compound 32 is coupled with the amino terminus of an ALA-PHE dipeptide (which has been protected with a benzyl group at the carboxyl terminus) using EDC and triethylamine to give compound 33. Removal of the benzyl protecting groups on 33 with hydrogen and palladium hydroxide over carbon in ethanol yields 34. The amino terminus of 34 is then reacted with succinimidyl hemiglutarylchloride in pyridine to give the hapten 35. The hapten, 35, can be coupled to the carrier protein, keyhole limpet hemocyanin. This carrier protein-hapten conjugate can then be used to induce antibodies that can be assayed for their ability to deamidate ASN 71 of triosephosphate isomerase and form the α-linked or β-linked ASP-GLY sequence.

It is important to note that this is just one specific example. A hapten can be built that will deamidate and isomerize any ASN-GLY containing peptide or protein so long as the sequence of amino acids that are flanking the ASN-GLY sequence is known. The target may be any protein or peptide such as an enzyme (like triosephosphate isomerase) or a receptor or coat protein of a virus or bacterium. Thus, antibodies induced from such a hapten have the ability to deamidate and isomerize the target protein and render the enzyme and/or virus/bacterium ineffective.

Example 2

Preparation of hybridomas which secrete monoclonal antibodies that catalyze the deamidation of a synthetic asparaginyl-glycyl substrate:

Monoclonal antibodies to the peptidomimetic phospholane hapten RG2 are produced using standard techniques. Many of the details of the procedure can be found in, for example, Benkovic et al., U.S. Pat. No. 5,079,152, which is hereby incorporated by reference.

As noted above, an immunogen is prepared by coupling the RG2 hapten to an antigenic carrier. Useful antigenic carriers are proteins such as keyhole limpet hemocyanin (KLH), edestin, albumins, such as bovine or human serum albumin (BSA or HSA), tetanus toxoid, and cholera toxoid, polyaminoacids, such as poly(D-lysine-D-glutamic acid), as well as red blood cells, such as sheep erythrocytes (SRBC).

In this Example, the RG2 hapten is coupled to KLH by reaction of the free carboxylate with sulfo-N-hydroxy succinimide which is then reacted with KLH. A description of the procedure is as follows:

The immunogenic conjugate is then used to raise monoclonal antibodies according to per se known methods as described, for example, by Niman et al., Proc. Natl. Acad. Sci. USA 7:4524 (1980); Niman et al., in "Monoclonal Antibodies and T-cell Products, ed. Katz, O.H., pp. 23–51, c. 1982 by CRC Press, Boca Raton, Fla.; and Kohler et al., Nature 256:495 (1975); all of which are hereby incorporated by reference.

Four mice (strain 129GIX) are immunized with the hapten conjugated to the carrier protein. The immunization dosage was 100 μg of the KLH-hapten conjugate in an adjuvant medium (CPBS/Freunds or RIBIS), injected every 2 weeks for 6 weeks. Two months later, before fusion, 50 μg of the conjugate in PBS were injected. The spleens are isolated and hybidomas are prepared by fusion of the spleen cells with mouse myeloma cells (cell line SP/20).

Example 3

Figure 8:
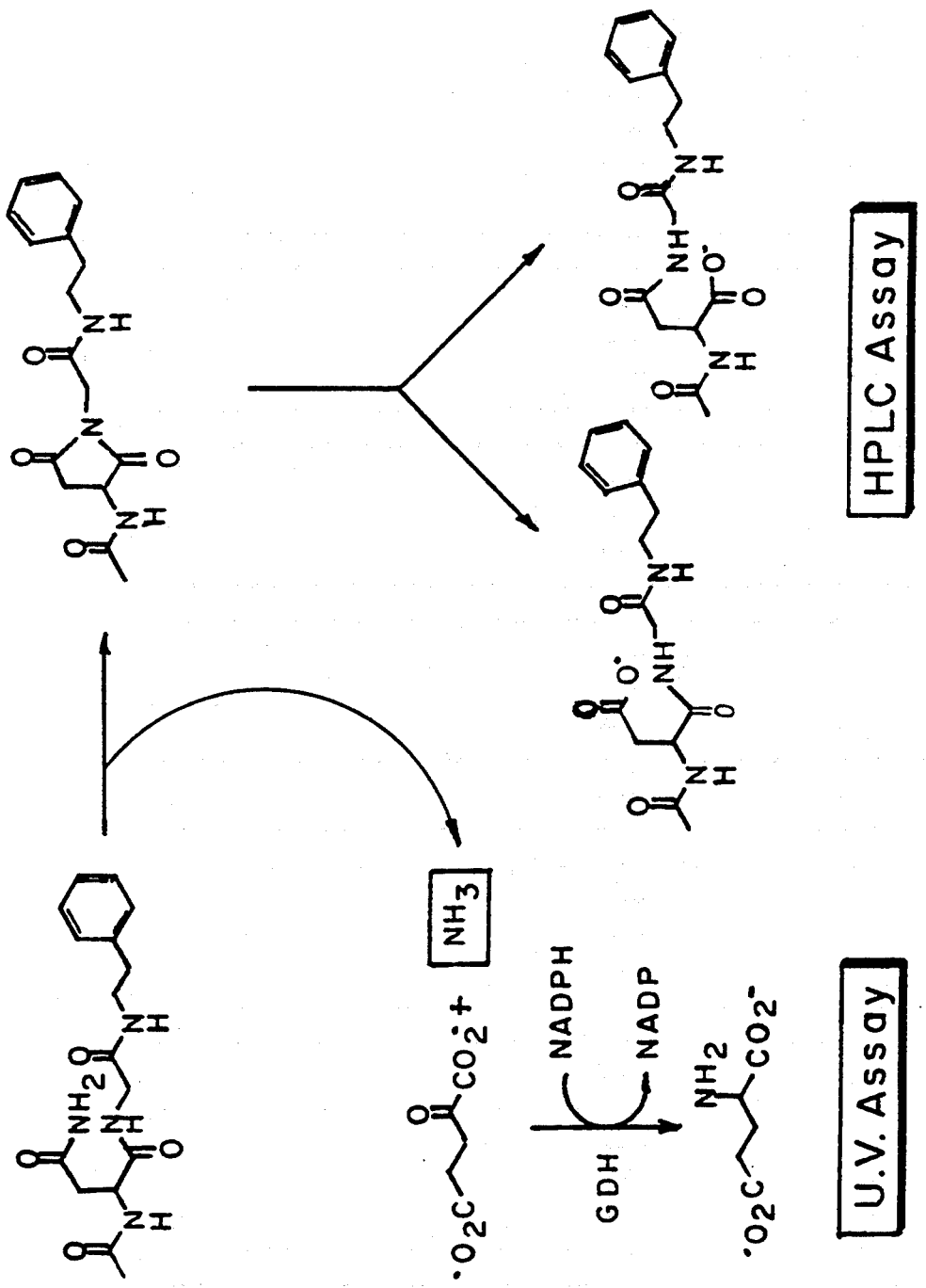

Assay and Screening of Hybridomas for Antibodies Which Catalyze the Deamidation Reaction The resulting hybridomas are subjected to a preliminary screening for binding to the hapten using standard methods specifically as described in U.S. Pat. No. 5,079,152 to Benkovic et al, noted above. Those hybridomas demonstrating specific binding to the hapten are cloned and re-screened for the production of monoclonal antibodies which catalyze the deamidation of the phenyl ethyl derivative of the asparaginyl-glycyl dipeptide by an assay as shown in FIG. 8. This assay is chosen to specifically screen for those antibodies which catalyze the deamidation reaction and assays by the determination of ammonia. The procedure is a modification of known procedures which use glutamate dehydrogenase to detect ammonia. (See Foncesca-Wollheim, F. Clin. Chem., 3336/8, 1483–1487 (1990), and von Anken, H. D., Schiphorst, M. E., Clinica Chimica Acta, 56, 151–157 (1974)).

The deamidation to the cyclic imide intermediate is assayed by a spectrophotometric procedure coupling the antibody-catalyzed reaction to the enzyme glutamate dehydrogenase. Glutamate dehydrogenase utilizes the ammonia produced from the antibody-catalyzed deamidation reaction to convert alpha-ketoglutarate into glutamic acid, oxidizing nicotimamide dinucleotide phosphate in the process (NADPH is oxidized to NADP). The glutamate dehydrogenase reaction is monitored spectrophotometrically.

Figure 9A:
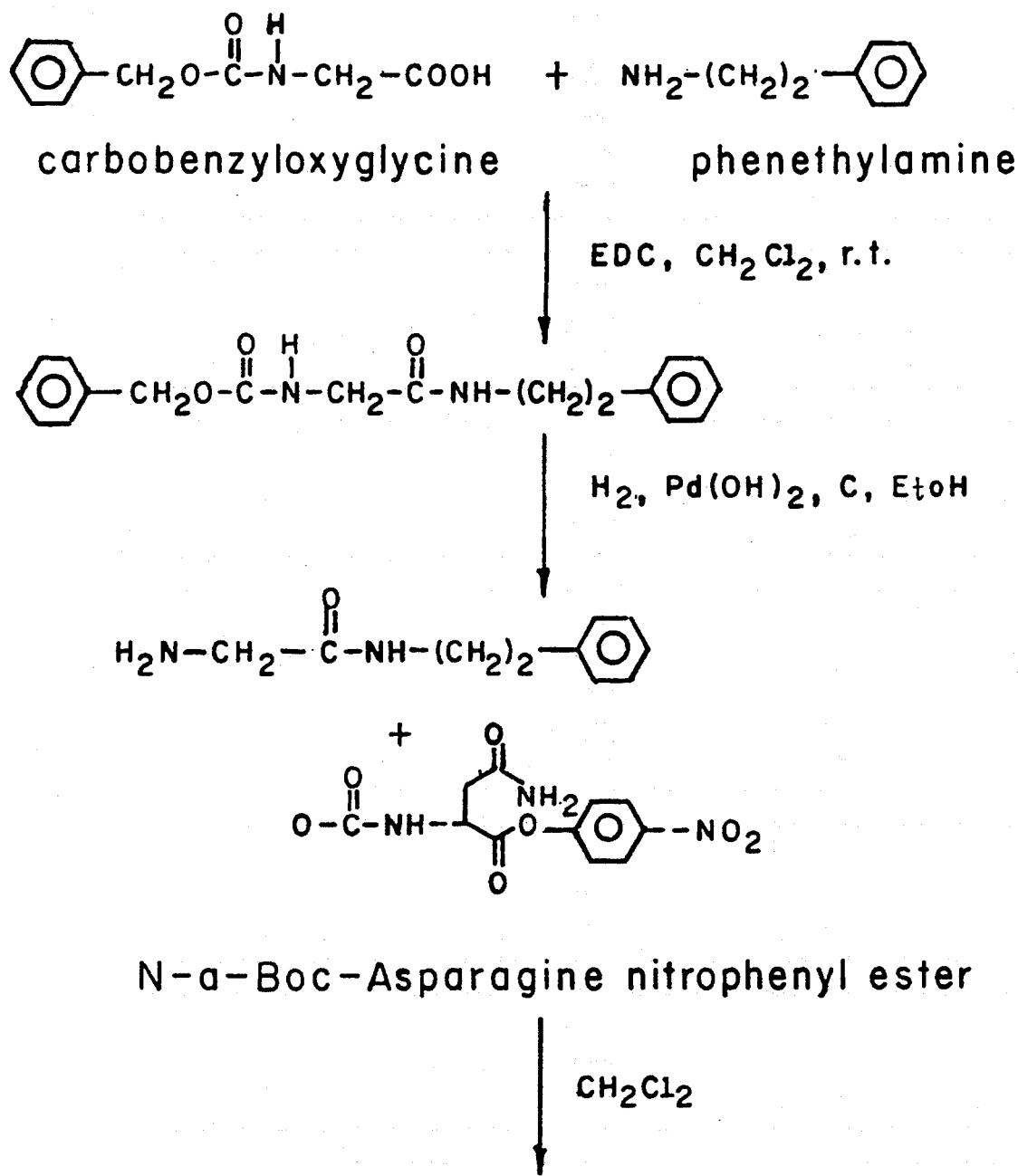
Figure 9B:
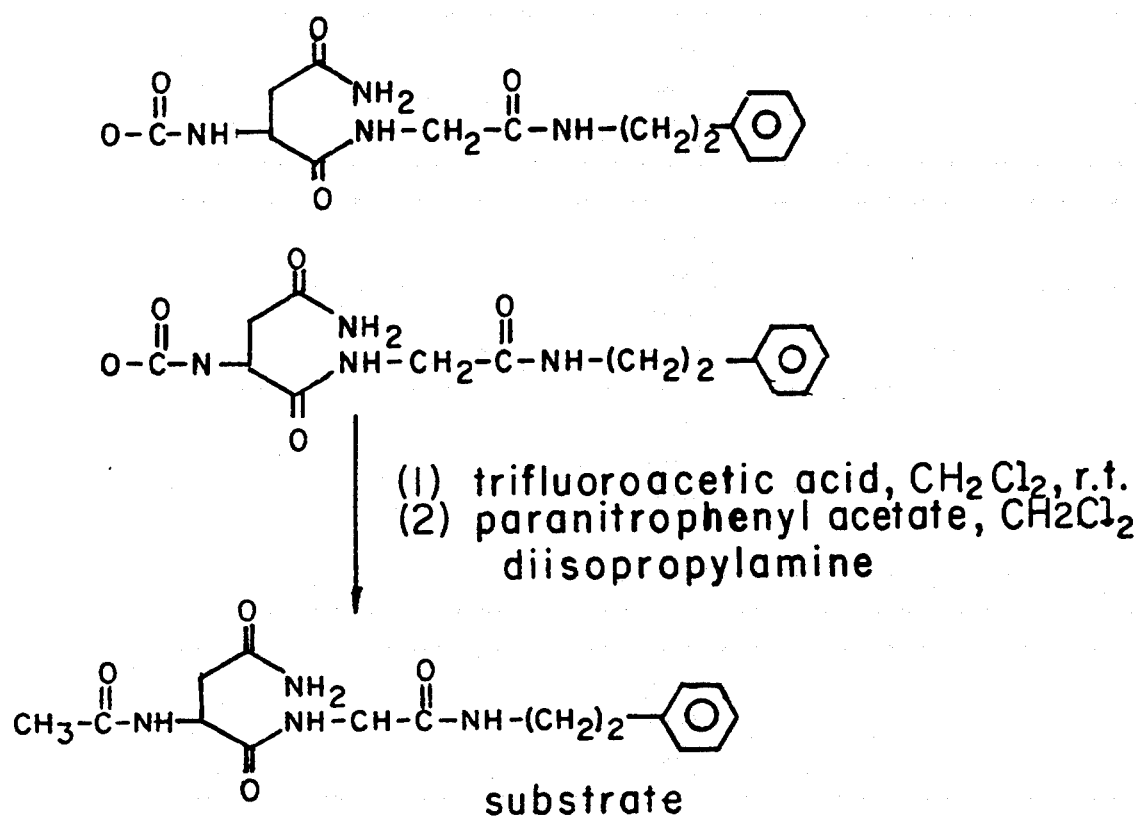

The substrate for the assay is first prepared by the process described in FIG. 9.

Thirty antibodies are picked for assay for catalytic activity. The antibodies are delivered in phosphate buffered saline solutions. These are then dialyzed into bicine buffer (pH 9.0, 0.10M) and 100 uL of the dialyzed solution was then added to a solution of bicine (166 uL, pH 9.0, 0.10M). To this is added 16.5 uL of a solution containing 400 uM NADPH, α-ketoglutarate, and adenosine diphosphate. This is mixed thoroughly and then 16.5 uL of analytical grade glutamate dehydrogenase (Boehringer Mannheim) is added and the solution is again mixed thoroughly. The reaction is initiated by addition of the substrate which is stored in a DMSO solution such that the total concentration of DMSO was 5%.

The solution is then transfered to a small cuvette and the decrease in absorbance at 340 nanometers is followed over a period of several hours. Control reactions are performed under identical conditions without the addition of antibody to the reaction mixture (bicine buffer was added in place of the antibody to maintain volume). The antibody catalyzed rate is determined by subtracting the overall rate (antibody-catalyzed and spontaneous rates) from the spontaneous rate determined from the control reaction.

The hydrolysis step is monitored by analyzing the product distribution using high perfomance liquid chromatography (HPLC). The procedure is as follows: 238 uL of the antibody (dialyzed from PBS into 0.10M bicine, pH 9.0) is added to an Eppendorf microcentrifuge tube. To this is added the substrate (as a DMSO solution) so that the total volume is 250 uL and the DMSO content is 5%. At various time intervals 50 uL samples are withdrawn from the reaction and quenched using 0.5 uL of 23% perchloric acid. The quenched sample is centrifuged for 2 minutes and then 20 uL is injected into the HPLC. Control reactions are performed under identical conditions without the addition of antibody (0.1M bicine, pH 9.0 was added instead). The conditions for the HPLC analysis are as follows:

Procedure: 238 uL of antibody (dialyzed form PBS into 100 mM bicine, pH 9) was added to an eppendorf micocentrifuge tube. To this was added 12.5 uL of a 10 mM solution of substrate in DMSO. The final concentration of substrate was 500 uM (total number of nmoles of substrate was 125 nmoles). The DMSO content was 5. The reaction was run at room temperature and at various time intervals 50 uL samples were withdrawn from the reaction and quenched with 0.5 uL 23% perchloric acid (the solution immediately became cloudy upon addition of perchloric acid). The quenched sample was centrifuged for 2 minutes and then 20 uL of this was injected into the HPLC. The conditions for the HPLC were as follows:

column: Vydac C18 Analytical (4.6 mm×25 cm)
UV: 254 nM
mobile phase:
 Soln. A: 0.1% TFA in water.
 Soln. B: acetonitrile.
flow rate: 1 mL/min
gradient used:

| time | % acetonitrile | % water/TFA |
| --- | --- | --- |
| initial | 5 | 95 |
| 5 | 15 | 85 |
| 30 | 40 | 60 |
| 35 | 100 | 0 |
| 40 | 100 | 0 |
| 45 | 5 | 95 |
| 60 | 5 | 95 |

The control was run under the exact same conditions except 238 uL of bicine buffer, 100 mM, pH 9 was used but did not contain antibody.

Analysis of the catalytic properties of 30 of the monoclonals obtained shows that six of them showed evidence of catalytic properties, as shown by the distribution of the products obtained from deamidation of the substrate by the antibodies. The products formed from the D- or L-isomer of the substrate are shown in Table I, as are the overall rates of reaction compared to the spontaneous reaction rate.

TABLE I

| Ab | Product Distribution IsoAsp/Asp Product Ratio | | Overall Rate Enhancement |
| --- | --- | --- | --- |
| | L-isomer | D-isomer | |
| 39F3 | 8.3 | (3.6)$^s$ | xx |
| 14A8 | (3.4)$^s$ | 1.4 | xx |
| 23C7 | 16.4 | 1.2 | xx |
| 40H4 | 1.9 | 5.7 | xx |
| 2E4 | 2.4 | 4.7 | xx* |
| 24C3 | 2.1 | 4.8 | xx* |

Figure 10:
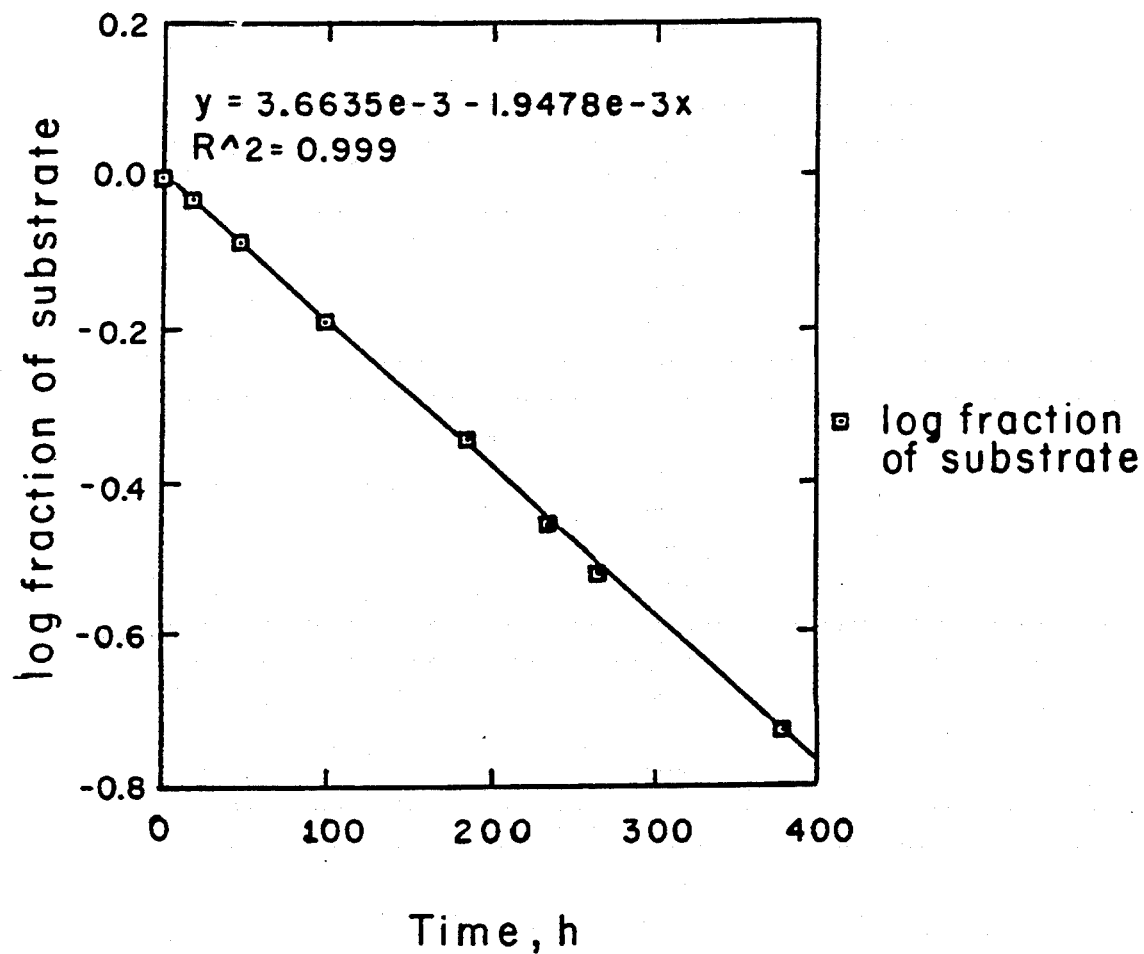
Figure 11:
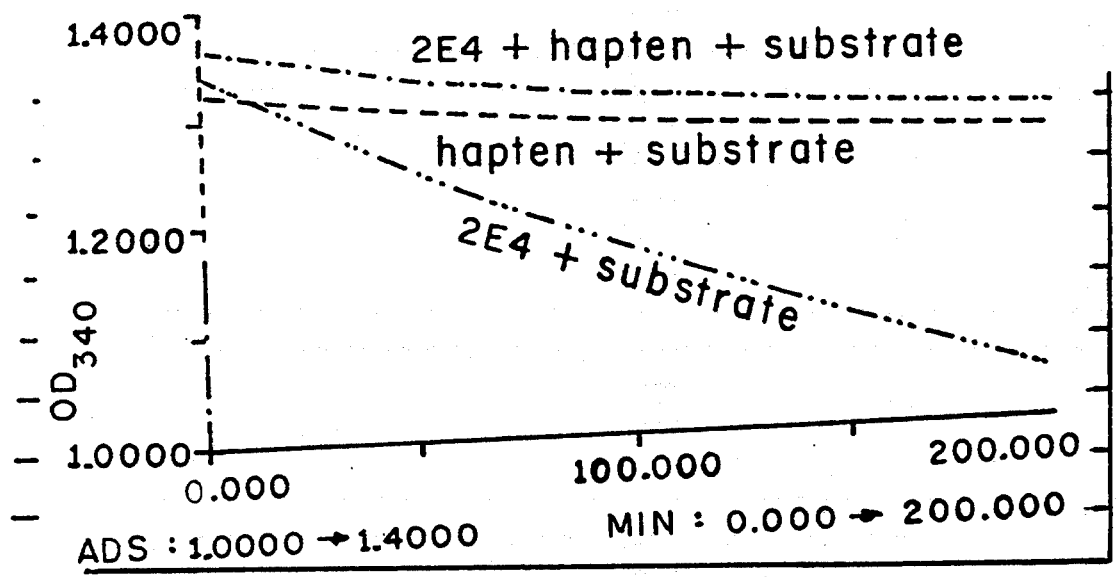
Figure 12:
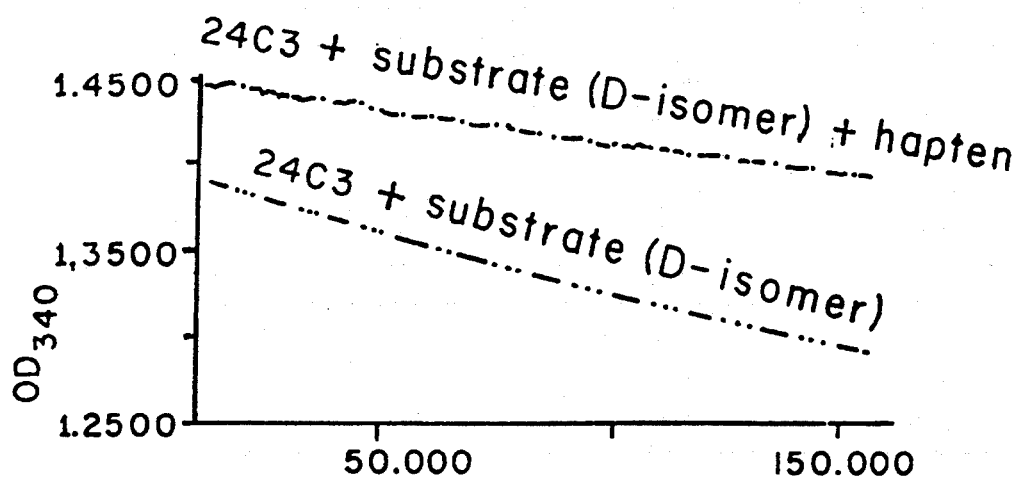

$^s$IsoAsp/Asp ratio for spontaneous reaction is 3.6
*found to be highly catalytic The spontaneous deamidation of the substrate, that is the reaction in the absence of any catalyst proceeds very slowly, having a half-time of approximately 5½ days and produces both the isoaspartic acid-glycyl dipeptide (isoDG) and the aspartic acid-glycyl dipeptide (DG) in a ratio of 3.6:1. Thus, this is the baseline against which the reaction rate and products of the deamidation catalyzed by the monoclonal antibodies must be compared. Kinetic data for the spontaneous hydrolysis of the substrate at pH 9.0 is shown in FIG. 10. This data was obtained using the HPLC assay without antibody present. The first-order rate constant and the half-life is given in the FIG. 10. Some raw kinetic data for antibodies 2E4 and 24C3 are shown in FIGS. 11 and 12. These were obtained using the glutamate dehydrogenase assay. These plots show the decrease in absorbance at 340 nM with time. This decrease is a result of NADPH being converted to NADP.

The plot for 2E4 has three lines on it: one is from the reaction of the antibody with substrate (steepest slope), one is from the spontaneous deamidation of the substrate without antibody but in the presence of hapten and the third shows the inhibition of the antibody reaction in the presence of hapteno The slopes of the lines are given in the Figure and kcat was calculated to be 0.416 h-1 (25° C.) for 2E4 (calculations not given) resulting in a rate enhancement of 92-fold. This is not a $V_{mx}$ since the substrate was not at total saturation of the antibody. The actual rate enhancement is probably greater. The assay conditions were as follows: 308 uL of 2E4 (5.9 mg/mL) in bicine buffer, pH 9.0, 0.1M; 45 uL of a solution (in water) containing ADP (12.0 mM), NADPH (2.4 mM) and α-ketoglutarate (120 mM); 24 uL glutamate dehydrogenase (Boehringer Mannheim cat. no. 127 710, 10 mG/mL, 120 units/mg); 46 uL hapten (1.17 mM solution in water) or 46 uL distilled water and 20 uL of substrate (10 mM solution in DMSO). The total volume of the assay was 443 uL. The final concentration of these compounds in the assay were: antibody, 27.4 uM; bicine, 70 mM; NADPH, 244 Um; ADP, 1.22 mM; α-ketoglutarate, 12.2 mM, hapten, 120 uM; substrate, 451 uM.

The plot for 24C3 has two lines on it: one is for the reaction of the antibody with substrate and the other shows the inhibition of this reaction with hapten. The slopes are given on the figure and the kcat is 0.352. The rate enhancement is about 77-fold. Again, this is not a true $V_{max}$ and the actual rate enhancement is probably greater.

The antibodies demonstrate some interesting properties. First of all, the antibodies produce isoDG:DG ratios quite different from the ratio produced by the spontaneous reaction. This ratio is different depending upon whether the D- or L- isomer of the amino acids are used in the substrate dipeptide. One class of antibody produced a skewed product ratio (compared to the spontaneous reaction) only with the L- isomer (39F3). A second class produced a skewed product ratio only with the D- isomer (14A8). A third class skewed the product ratio if either isomer is used (the remaining antibodies).

This third class may be further subdivided as to whether the isoDG:DG ratio is high or low depending upon the isomer and to what degree the ratio is changed from that observed for the spontaneous reaction. The antibody 23C7 produces a (very) high isoDG:DG ratio using the L-isomer and a low ratio using the D- isomer. In contrast, antibodies 40H4, 2E4 and 24C3 produce a low ratio using the L- isomer and a high ratio using the D- isomer.

The antibodies 2E4 and 24C3 have the interesting property that while the product distribution which they make is not too different from that of the spontaneous reaction, these antibodies are the most highly catalytic The reason for this is that it is the first step in the reaction (ring closure with loss of ammonia) that is rate limiting The other antibodies which more drastically affect the product ratio apparently affect the second step in the reaction more than the first. As the second step is already fast, the overall rate of the reaction is not so much affected; the influence of these catalysts is shown more in the alteration of the distribution of the products The reaction catalyzed by the 2E4 antibody was investigated in more detail. The binding affinity for the substrate ($K_m$) was determined to be $220 \pm 10$ $\mu M^{-1}$. $k_{cat}$ was determined as $1.5 \pm 0.3 \times 10^{-4}$, $s^{-1}$, approximately 120 times the rate for the spontaneous reaction The ratio of the catalytic rate constant to the substrate binding affinity (turnover rate; $k_{cat}/K_M$) for the antibody is $6.8 \times 10^{-7}$ $\mu M$ $s^{-1}$. Furthermore, the deamidation of the substrate catalyzed by the antibody is stoichiometrically inhibited by the phospholane hapten, indicating that the catalysis is not due to a contaminant arising from the process used to produce the antibody. General procedure for production of monoclonal antibodies catalyzing the inactivation of any desired target protein by deamidation of an asparaginyl-glycyl dipeptide moiety a) Identification of the Asn-Gly linkage:

When it is desirable to destroy to biological activity of a protein under physiological conditions, catalysis of the deamidation of an asparaginyl-glycyl dipeptide moiety within the polypeptide backbone is an effective means of doing so. Thus, described herein is a general procedure for the production of monoclonal antibodies to catalyze such deamidation in a specific protein target.

One begins with an analysis of the amino acid sequence of the target protein. Two conditions must be met by the structure of the target protein: (1) the amino acid sequence must contain an asparaginyl-glycyl dipeptide and (2) the asparaginyl-glycyl dipeptide must be localized on the surface of the protein when the protein assumes its active conformation. The amino acid sequence of a large number of proteins is available from the GENBANK database. If the sequence of the protein of interest is not contained in the database, then it can be determined by any of the methods commonly used to perform such analysis, such as Edman degradation of the purified protein. If the amino acid sequence is found to fulfill the first condition, the probability that the asparaginyl-glycyl dipeptide is localized on the surface of the protein can be evaluated by a hydropathicity analysis (Kyte, J. and Doolittle, R. F., J. Mol. Biol. 157:105 (1982)). This analysis can be done using a number of computer programs available (for example, "PEP" available from Intelligenetics, Mountain View, Calif.) that evaluate the degree of polarity of segments of the amino acid sequence, moving the "window" of the sequence evaluated along the length of the polypeptide. Portions of the protein found to be highly polar are assigned a high probability of surface localization, while portions found to be non-polar are assigned a low probability of surface localization. If condition (2) is found to be met, then the production of a catalytic antibody for the inactivation of the protein by deamidation asparaginyl-glycyl dipeptide is feasible.

b) Preparation of the desired hapten:

The next step in the production of the catalytically inactivating antibody is to synthesize a hapten which contains the phospholane peptidomimetic nucleus, which represents the transition states in the deamidation reaction, flanked by amino acids which are found surrounding the asparaginyl-glycyl dipeptide in the target protein. Such a synthesis is described above.

The hapten is then coupled to a carrier protein and used to immunize a mammal.

c) Preparation of monoclonal antibodies:

Spleen cells or other lymphoid tissues from the immunized animal are used as the antibody producing cells in the establishment of a population of cell lines secreting monoclonal antibodies. Two methods for doing this are well-established, creation of hybridomas by fusion of spleen cells with a myeloma cell line and immortalization of antibody producing B cells by transformation with Epstein-Barr virus.

d) Screening of cell lines for catalytically active antibodies:

The population of cell lines secreting a population of monoclonal antibodies is then screened to identify those cell lines which are producing antibodies which exhibit catalytic activity in the deamidation of the asparaginyl-glycyl dipeptide. This screening may be done directly for individual antibodies as described above or may be accomplished in several steps. The latter is described in the following.

In order to identify the cell lines which show the most promise of providing a catalytic antibody, it is useful to screen the population for antibodies which bind the hapten. This can be accomplished using a standard immunoassay by coupling the hapten to a labeled protein which is different both from the carrier protein used in the immunization and from the target protein. The carrier used for screening must be different from both of these proteins to avoid artifacts arising from recognition by the antibodies of epitopes other than the hapten mimicked portion of the target protein. It should be understood, however, that mere binding of the hapten is not a demonstration of catalytic activity in the deamidation reaction. Thus, the population of cell lines which produce antibodies that bind the hapten must be screened further to demonstrate catalytic activity.

Such screening can be accomplished using the assays described above. Antibodies which can catalyze the deamidation of the model substrate must then be assayed for their ability to inactivate the actual protein target. Clearly the assay used will be dependent upon the nature of the target protein, but will consist at least of incubating the antibody with the target protein and then assaying the biological activity. Useful procedures for assaying for activity of a target protein will be known to those skilled in the art and will, of course, depend upon the specific activity of the target protein. For example, if the target protein is a virus which is cytotoxic, the proliferation of the host cell line can be measured after infecting the cells with virus which is exposed to the antibody. An obvious negative control experiment is the substitution of the antibody by the assay buffer. It is also desirable to assess the specificity of the reaction by measuring the inactivation of a second target protein, which also contains a surface localized asparaginyl-glycyl dipeptide, but otherwise does not resemble the target protein.

A positive control is measuring the inhibition by the hapten of the inactivation of the protein by the antibody. In order to conclude that the inactivation is in fact caused by catalytic action of the antibody, kinetic measurements of the inactivation process should show that the hapten acts as a competitive inhibitor of the inactivation of the target protein.

Upon identification of cell lines which are catalytic inactivators of the target protein, the monoclonal antibodies can be characterized and purified from supernatants of cultures of the cells by any of the well-known techniques for accomplishing the purification. For example, the immunoglobulin class can be determined by testing for reaction with anti-IgG or anti-IgM (or other class and sub-class specific) antibodies. If the monoclonal antibody is found to be of the IgG type, it can be purified from the culture supernatants by affinity purification using immobilized protein G (for example, Bethesda Research Laboratories catalog number 5921SA). Alternatives to Standard Hybridoma Technology and Monoclonal Antibodies:

As described above, recent advances in understanding antibodies has led to alternative procedures whereby, instead of monoclonal antibodies, Fab proteins specific for desired targets can be prepared. This technology can also be put to use in the present invention for the preparation of Fab proteins which can catalyze deamination of protein.

a) Production in $E.\ coli$ of Fab proteins catalyzing the deamidation of an asparaginyl-glycyl dipeptide:

The production of proteins which have catalytic activity that are made by expressing the antigen binding portion of antibodies in a bacterial host cell has been previously described (L. Sastry et al., Proc. Natl. Acad. Sci. 86:5728 (1989); W. D. Huse et al., Science 246:1275 (1989)). These methods can also be used to produce proteins which catalytically deamidate asparaginyl-glycyl dipeptides.

The details of the materials and methods for accomplishing the production of particular Fab proteins will of course depend upon the properties one desires in the final product. For instance, the following describes the production of an Fab product containing a decapeptide tag useful for affinity purification of the Fab protein. Clearly, the identity of this tag may be varied, almost at random. Also, the following describes the use of a particular λ-phage vector to accomplish the cloning and expression. The choice of the vector is not a limitation of the process, nor is the expression of both the heavy and light chain genes from a single vector. It is possible that each gene could be carried by a separate vector and introduced together into a single host cell.

Generally, the requirements of the system are that the vector must contain the DNA elements neccessary for the expression of the antigen-binding portion of the antibody heavy chain gene from the cloned DNA sequence which encodes that protein. The vector must also contain the DNA elements neccessary for the expression of the antigen-binding portion of the light chain gene from the cloned DNA sequence which encodes the light chain-derived protein. In the case of presently described system, these elements are (1) a ribosome binding site coupled to (2) a leader sequence of amino acids which directs translation initiation and secretion of the protein product; in this instance, the leader sequence is derived from the bacterial pelB gene, which has been previously found successful in the secretion of Fab proteins (M. Berrer et al., Science 240:1041 (1988); A. Skerra and A. Pluckrhun, ibid. p. 1038)). The pelB leader sequence is followed by restriction sites suitable for inserting the light chain or heavy chain gene fragment. In a first vector for cloning of the heavy chain gene fragment, these restriction sites are XhoI and SpeI, which are also incorporated in the oligonucleotide primers used to amplify the V region of the heavy chain genes from spleen cell mRNA (described below).

In a second vector for the cloning of the light chain gene fragment, the sites are SacI and XbaI, which are similarly included in the amplification primers used to obtain the DNA for cloning the V region of the light chain genes. In the vector for the cloning the heavy chain gene fragment, a decapeptide, having the amino acid sequence YPYDVPDYGS, (SEQ. I.D. NO. 2), is inserted immediately downstream of the SpeI site to provide a tag for affinity purification of the final Fab product using a monoclonal antibody directed to the decapeptide. A stop codon is present following the decapeptide in the vector for cloning the heavy chain gene fragments; the stop codon immediately follows the XbaI site in the vector for cloning light chain gene fragments. The entire expression cassettes are flanked on one side by an EcoRI site and on the other by a NotI site. These flanking sites are arranged in opposite orientations in the two vectors to allow for in vitro recombination of the two cloned libraries to form a single library of combinatorially joined sequences which contain a heavy chain gene fragment and a light chain gene fragment in a single λ-phage vector. In the present case all of these elements are introduced into a λ ZAP vector from Stratagene (San Diego, Calif.).

After cloning of the heavy chain gene fragments and the light chain gene fragments into individual λ libraries, DNA representing the entire light chain library is isolated and cleaved with MluI and then the 5'-ends of the resulting fragments are dephosphorylated. Similarly, the DNA representing the entire light chain library is cleaved with HindIII and the 5'-ends of the fragments are dephosphorylated. The products of each of these digests are then cleaved with EcoRI and mixed and ligated. After ligation, only clones that result from combination of a right arm of light chain-containing clones and a left arm of heavy chain-containing clones reconstitute a viable phage. The ligation mixture is then packaged in vitro and used to infect a suitable E. coli host cell strain.

Figure 13A:
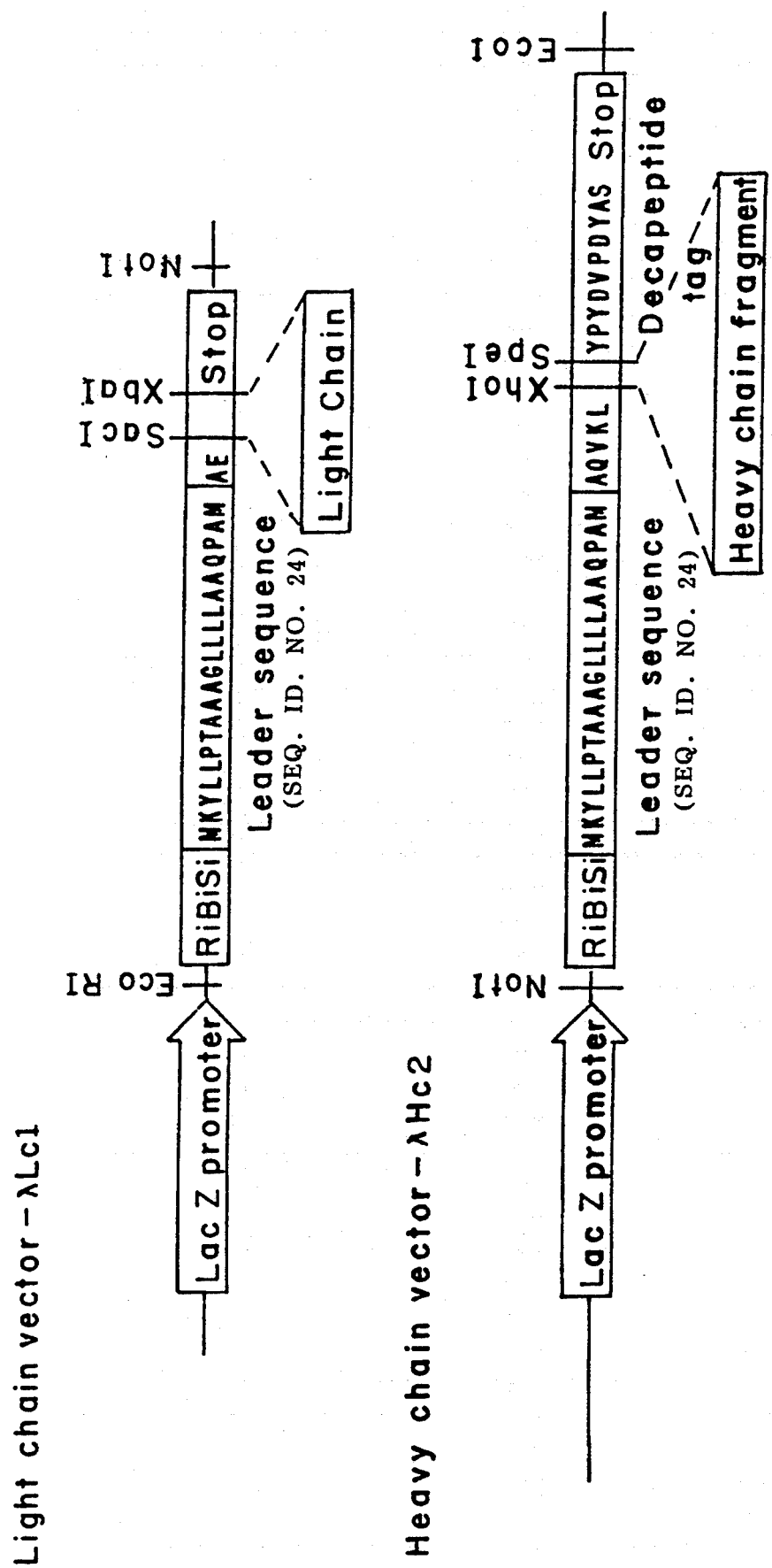
Figure 13B:
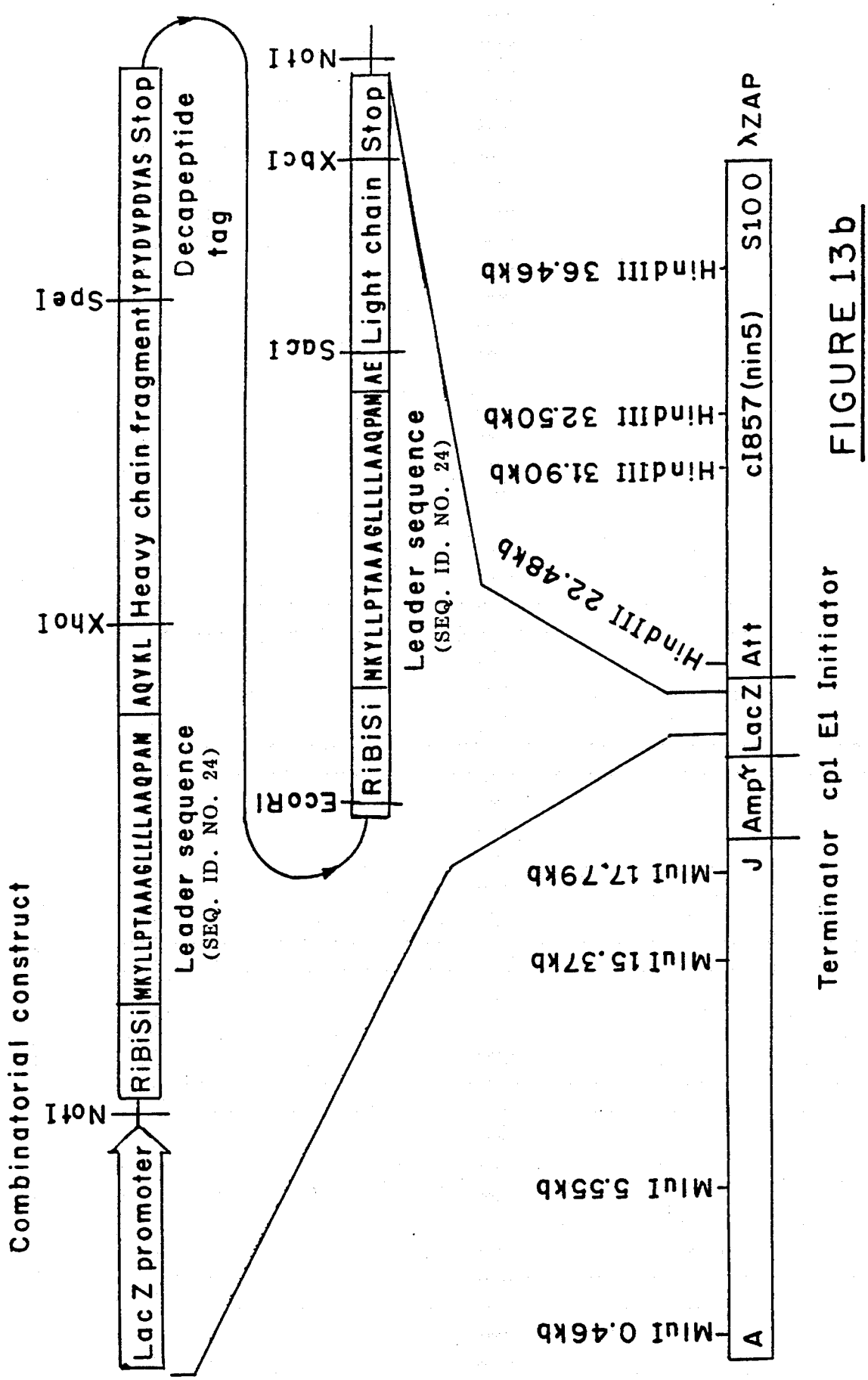

The λ vectors described above are shown schematically in FIG. 13. The ribosome binding site-leader sequence encoding DNA fragments are shown in FIG. 14. The complete vector system is commercially available from Stratagene.

The DNA fragments to be inserted into the vectors are most conveniently obtained by PCR amplification of mRNA transcribed from the rearranged immunoglobulin genes found in spleen cells of immunized animals. The immunization increases the proportion of mRNA which represents sequences that encode immunogen recognizing antibodies, but is an optional step. Primers for the PCR amplification are designed from the sequences of the conserved regions of the immunoglobulin gene sequences which flank the $V_H$ domains (R. Orlandi et al., Proc. Natl. Acad. Sci. 86:3833 (1989)). For amplification of the $V_H$ domain, the 3' primer is designed to be complementary to the mRNA of the J region of the immunoglobulin mRNA. The 5' primers are designed to be complementary to the antisense strand (first strand of cDNA) of the conserved N-terminal region of the immunoglobulin mRNA. The primers also incorporate restriction sites for cloning in the appropriate reading frame into the vectors described above (XhoI for the 5'primer, SpeI for the 3' primer for heavy chain amplification). The 3' primer also contains a sequence encoding a cysteine residue so as to allow disulfide linking of the heavy and light chain fragments as they are synthesized by the bacteria. The primers for the light chain amplification are designed using similar principles.

For the production of libraries from mice, primers which are useful for the amplification of the $F_d$ ($V_H$ to $C_1$ region) and $F_v$ encoding regions of the immunoglobulin heavy chain mRNA are shown in Table II. Primers that are useful for amplification of the $F_v$ encoding region of the kappa light chain are shown in Table III. For production of libraries from mouse mRNA, cloning of lambda light chain genes is not required, as they are represented in only a small portion of the expressed immunoglobulins in mice.

TABLE II

| HEAVY CHAIN PRIMERS | |
|---|---|
| 1) 5'-AGGT A CT CTCGAGTC GG-3' | (SEQ ID NO: 3) |
| 2) 5'-AGGTCCAGCTGCTCGAGTCTGG-3' | (SEQ ID NO: 4) |
| 3) 5'-AGGTCCAGCTGCTCGAGTCAGG-3' | (SEQ ID NO: 5) |
| 4) 5'-AGGTCCAGCTTCTCGAGTCTGG-3' | (SEQ ID NO: 6) |
| 5) 5'-AGGTCCAGCTTCTCGAGTCAGG-3' | (SEQ ID NO: 7) |
| 6) 5'-AGGTCCAACTGCTCGAGTCTGG-3' | (SEQ ID NO: 8) |
| 7) 5'-AGGTCCAACTGCTCGAGTCAGG-3' | (SEQ ID NO: 9) |
| 8) 5'-AGGTCCAACTTCTCGAGTCTGG-3' | (SEQ ID NO: 10) |
| 9) 5'-AGGTCCAACTTCTCGAGTCAGG-3' | (SEQ ID NO: 11) |
| 10) 5'-AGGTTTATCTTCTCGAGTC GG-3' | (SEQ ID NO: 12) |
| 11) 5'-CTATTAACTAGTAACGGTAACAGTGGTGCCTTGCCCCA-3' | (SEQ ID NO: 13) |
| 12) 5'-AGGCTTACTAGTACAATCCCTGGGCACAAT-3' | (SEQ ID NO: 14) |

TABLE III

| LIGHT CHAIN PRIMERS | |
|---|---|
| 1) 5'-CCAGTTCCGAGCTCGTTGTGACTCAGGAATCT-3' | (SEQ ID NO: 15) |
| 2) 5'-CCAGTTCCGAGCTCGTGTTGACGCAGCCGCCC-3' | (SEQ ID NO: 16) |
| 3) 5'-CCAGTTCCGAGCTCGTGCTCACCCAGTCTCCA-3' | (SEQ ID NO: 17) |
| 4) 5'-CCAGTTCCGAGCTCCAGATGACCCAGTCTCCA-3' | (SEQ ID NO: 18) |
| 5) 5'-CCAGATGTGAGCTCGTGATGACCCAGACTCCA-3' | (SEQ ID NO: 19) |
| 6) 5'-CCAGATGTGAGCTCGTCATGACCCAGTCTCCA-3' | (SEQ ID NO: 20) |
| 7) 5'-CCAGTTCCGAGCTCGTGATGACACAGTCTCCA-3' | (SEQ ID NO: 21) |
| 8) 5'-GCAGCATTCTAGAGTTTCAGCTCCAGCTTGCC-3' | (SEQ ID NO: 22) |
| 9) 5'-GCGCCGTCTAGAATTAACACTCATTCCTGTTGAA-3' | (SEQ ID NO: 23) |

After obtaining the library of clones expressing Fab proteins, the library is screened to identify those clones which are producing Fab proteins which bind to the phospholane peptidomimetic hapten. This may be accomplished by plating the phage and immobilizing the proteins in the plaques on a filter. The filter is then hybridized with a labelled protein to which the hapten has been covalently attached. As described above, the carrier protein used in screening should differ from both the carrier protein used to immunize the animal from which the antibody gene encoding DNA is obtained (if such immunization is performed) and from any target protein which it is desired to inactivate by the deamidation reaction. The label used to tag the protein can be a radioisotope, biotin, or other specifically detectable label.

To identify those Fab proteins which exhibit catalytic activity in the deamidation of an asparaginyl-glycyl dipeptide, the Fab proteins are expressed in large scale in the bacteria and purified by affinity chromatography of the decapeptide tag. The purified Fab proteins are then used in the assay described above for the assessment of catalytic activity in monoclonal antibodies.

b) Production of proteins catalyzing the deamidation of an asparaginyl-glycyl dipeptide in the coat of filamentous bacteriophages:

An alternative to the expression of the Fab protein within the bacterial cell is the expression of the protein in the coat of a filamentous bacteriophage which is secreted from the bacterium. This has the advantage that the protein is made in a particle which also contains instructions for its synthesis (A.S. Kang et al., Proc. Natl. Acad. Sci. 88:4363 (1991)).

From a λ-phage library constructed as above in (a), the cassette of DNA encoding the Fab protein can be modified by removal of the decapeptide tag, replacing it with DNA encoding a coat protein of a filamentous bacteriophage. The modified cassette can then be re-cloned into a vector derived from a filamentous bacteriophage. Such a vector, following transformation into a suitable bacterial host cell strain, will produce filamentous bacteriophage particles which incorporate the Fab protein into the coat of the phage and package the vector DNA within the phage particle. If done with the DNA from a clone already known to encode a catalytic Fab protein, further screening is neccessary only to assure that the addition of the coat protein localizing sequence does not disrupt the activity. Alternatively, the cassette can be modified prior to the screening step and the screening can be performed upon the whole population of filamentous phages. The filamentous phage system provides the advantage that the instructions for producing the catalytic Fab are present within the particle that displays the Fab its outer surface. Thus, the bacteriophage which produce Fab molecules that bind the hapten can be purified from the entire population by fixing the hapten to an insoluble support and affinity purifying hapten-binding phages. These phages can then be used to infect a fresh batch of host cells. This procedure allows very simple isolation of those phages which contain hapten-binding Fab molecules. Furthermore, if a particular Fab is found which displays desirable, yet sub-optimal characteristics, the phage can be subjected to mutagenesis and the mutant phages rescreened for the more optimal characteristic. Mutant phages displaying Fab having the more optimal characteristic are then purified, providing a stock of genetic material encoding an optimal Fab protein.

To provide a filamentous bacteriophage displaying Fab molecules which deamidate an asparaginyl-glycyl dipeptide, plasmid DNA from clones isolated as above is purified following in vitro excision from the λZAP host phage, as described by the the manufacturer (Stratagene). The decapeptide encoding portion of the cloned DNA is excised by digestion with EcoRI and SpeI and in its place the M13 phage coat protein VIII is inserted. The NotI fragment encoding the Fab protein is purified and inserted into the NotI site of the Bluescript phagemid vector and transformed into *E. coli* XL1-Blue cells (Stratagene). Colonies containing inserted DNA are identified by their white color and the plasmid DNA is characterized by restriction digestion. Clones containing plasmids having the proper structure are grown in super broth containing 50 μg/ml tetracycline (to select for the F' episome) to an $OD_{600}$ and infected with R408 or VCS M13 helper phage (phage:cell ratio is 10 to 20:1) and grown for a further 2 hours at 37° C. The cells are pelleted and the supernatants are assayed for expression of Fab proteins exhibiting catalysis of the deamidation of an asparaginyl-glycyl dipeptide substrate as described above. Phages are purified from the supernatants identified as containing catalytic Fab by precipitation with polyethylene glycol from a high salt buffer.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

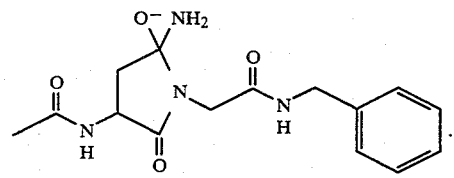

What is claimed is:

1. An antibody or fragment thereof having catalytic activity which catalyzes the deamidation reaction of the asparagine residue of an asparaginyl-glycyl dipeptide moiety.

2. The antibody or fragment thereof according to claim 1, which specifically binds to a transition state molecule of said deamidation reaction.

3. The antibody or fragment thereof according to claim 2, which specifically binds to a compound of the formula

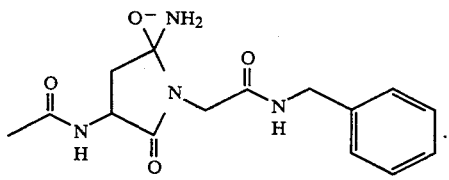

4. The antibody or fragment thereof according to claim 2, wherein said antibody or fragment thereof specifically binds to a compound of the formula

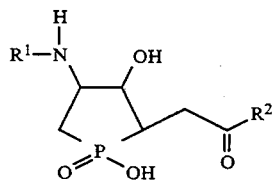

wherein $R^1$ and $R^2$ are the same or different and are oligopeptides of two to seven amino acids each.

5. The antibody or fragment thereof according to claim 4, wherein said antibody or fragment thereof is a monoclonal antibody or a Fab protein.

6. The antibody or fragment thereof according to claim 2, which does not bind to asparagine, glycine, aspartic acid or isoaspartic acid.

7. The antibody or fragment thereof according to claim 1, which is a monoclonal antibody or a Fab protein.

8. The antibody or fragment thereof according to claim 2, which is a monoclonal antibody or a Fab protein.

9. The antibody or fragment thereof according to claim 3, which is a monoclonal antibody or a Fab protein.

10. The antibody or fragment thereof according to claim 1, which specifically binds to a compound of the formula

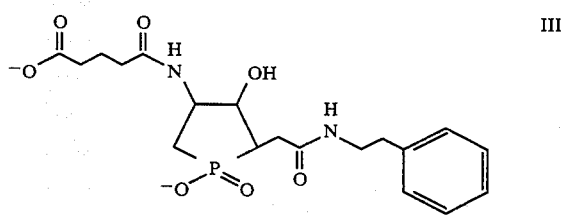

or a salt thereof.

11. The antibody or fragment thereof according to claim 10, which is a monoclonal antibody or a Fab protein.

12. An antibody or fragment thereof having catalytic activity which catalyzes the deamidation reaction of the asparagine residue of an asparaginyl-glycyl dipeptide moiety, wherein said antibody or fragment thereof does not bind to asparagine, glycine, aspartic acid, or isoaspartic acid.

13. A method for catalyzing the deamidation of the asparagine residue of an asparaginyl-glycyl dipeptide moiety which comprises exposing said moiety to an antibody or fragment thereof according to claim 1.

14. A method for catalyzing the deamidation of the asparagine residue of an asparaginyl-glycyl dipeptide moiety which comprises exposing said moiety to an antibody or fragment thereof according to claim 3.

15. A method for catalyzing the deamidation of the asparagine residue of an asparaginyl-glycyl dipeptide moiety which comprises exposing said moiety to an antibody or fragment thereof according to claim 9.

16. A method for catalyzing the deamidation of the asparagine residue of an asparaginyl-glycyl dipeptide moiety which comprises exposing said moiety to an antibody or fragment thereof according to claim 10.

17. A method for catalyzing the deamidation of the asparagine residue of an asparaginyl-glycyl dipeptide moiety which comprises exposing said moiety to an antibody or fragment thereof according to claim 11.

18. A method for catalyzing the deamidation of the asparagine residue of an asparaginyl-glycyl dipeptide moiety, wherein said moiety is a part of a polypeptide comprising $R^1$-asparaginyl-glycyl-$R^2$, wherein $R^1$ and $R^2$ are the same or different and are polypeptidyl groups, comprising exposing said polypeptide to a deamidating antibody or fragment thereof according to claim 4.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

Val Thr Asn Gly Ala Phe
1               5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Tyr Pro Tyr Asp Val Pro Asp Tyr Gly Ser
1               5                   10

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:3:

AGGTACTCTC GAGTCGG      17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:4:

AGGTACTCTC GAGTCGG      17

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:5:

AGGTCCAGCT GCTCGAGTCT GG      22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:6:

AGGTCCAGCT GCTCGAGTCA GG      22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:7:

AGGTCCAGCT TCTCGAGTCT GG                        22

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:8:

AGGTCCAGCT TCTCGAGTCA GG                        22

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:9:

AGGTCCAACT GCTCGAGTCT GG                        22

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:10:

AGGTCCAACT TCTCGAGTCT GG                        22

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:11:

AGGTCCAACT TCTCGAGTCA GG                        22

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:12:

AGGTTTATCT TCTCGAGTCG G                                                                 21

( 2 ) INFORMATION FOR SEQ ID NO:13:

( i ) SEQUENCE CHARACTERISTICS:
        ( A ) LENGTH: 38 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:13:

CTATTAACTA GTAACGGTAA CAGTGGTGCC TTGCCCCA                                                38

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:14:

AGGCTTACTA GTACAATCCC TGGGCACAAT                                                         30

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:15:

CCAGTTCCGA GCTCGTTGTG ACTCAGGAAT CT                                                      32

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:16:

CCAGTTCCGA GCTCGTGTTG ACGCAGCCGC CC                                                      32

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:17:

CCAGTTCCGA GCTCGTGCTC ACCCAGTCTC CA                                                      32

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:18:

CCAGTTCCGA GCTCCAGATG ACCCAGTCTC CA        32

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:19:

CCAGATGTGA GCTCGTGATG ACCCAGACTC CA        32

( 2 ) INFORMATION FOR SEQ ID NO:20:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:20:

CCAGATGTGA GCTCGTCATG ACCCAGTCTC CA        32

( 2 ) INFORMATION FOR SEQ ID NO:21:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:21:

CCAGTTCCGA GCTCGTGATG ACACAGTCTC CA        32

( 2 ) INFORMATION FOR SEQ ID NO:22:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:22:

GCAGCATTCT AGAGTTTCAG CTCCAGCTTG CC        32

( 2 ) INFORMATION FOR SEQ ID NO:23:

( i ) SEQUENCE CHARACTERISTICS:
        ( A ) LENGTH: 34 base pairs
        ( B ) TYPE: nucleic acid
        ( C ) STRANDEDNESS: both (D) TOPOLOGY: linear (i i) MOLECULE TYPE: DNA (genomic)

(x i) SEQUENCE DESCRIPTION: SEQ ID NO:23:

GCGCCGTCTA GAATTAACAC TCATTCCTGT TGAA            34